(12) United States Patent
Mizushima et al.

(10) Patent No.: US 9,221,786 B2
(45) Date of Patent: Dec. 29, 2015

(54) 2-FLUOROPHENYL PROPIONIC ACID DERIVATIVES

(71) Applicant: LTT BIO-PHARMA CO., LTD., Minato-ku, Tokyo (JP)

(72) Inventors: Toru Mizushima, Tokyo (JP); Masami Otsuka, Tokyo (JP); Yoshinari Okamoto, Tokyo (JP); Naoki Yamakawa, Tokyo (JP)

(73) Assignee: LTT Bio-Pharma Co., Ltd., Tokyo (JP)

( * ) Notice: Subject to any disclaimer, the term of this patent is extended or adjusted under 35 U.S.C. 154(b) by 0 days.

(21) Appl. No.: 14/369,106

(22) PCT Filed: Dec. 6, 2012

(86) PCT No.: PCT/JP2012/081646
§ 371 (c)(1),
(2) Date: Jun. 26, 2014

(87) PCT Pub. No.: WO2013/099553
PCT Pub. Date: Jul. 4, 2013

(65) Prior Publication Data
US 2014/0330026 A1 Nov. 6, 2014

(30) Foreign Application Priority Data
Dec. 27, 2011 (JP) .................................. 2011-285854

(51) Int. Cl.
| | | |
|---|---|---|
| *C07D 333/24* | (2006.01) | |
| *C07D 307/54* | (2006.01) | |
| *C07C 205/56* | (2006.01) | |
| *C07C 309/65* | (2006.01) | |
| *C07C 323/62* | (2006.01) | |
| *C07C 229/42* | (2006.01) | |
| *C07C 69/65* | (2006.01) | |
| *C07C 69/732* | (2006.01) | |
| *C07C 69/757* | (2006.01) | |
| *C07C 59/215* | (2006.01) | |
| *C07C 69/67* | (2006.01) | |
| *C07C 59/72* | (2006.01) | |
| *C07C 59/88* | (2006.01) | |
| *C07C 59/90* | (2006.01) | |

(52) U.S. Cl.
CPC ............ *C07D 333/24* (2013.01); *C07C 59/215* (2013.01); *C07C 59/72* (2013.01); *C07C 59/88* (2013.01); *C07C 59/90* (2013.01); *C07C 69/65* (2013.01); *C07C 69/67* (2013.01); *C07C 69/732* (2013.01); *C07C 69/757* (2013.01); *C07C 205/56* (2013.01); *C07C 229/42* (2013.01); *C07C 309/65* (2013.01); *C07C 323/62* (2013.01); *C07D 307/54* (2013.01); *C07C 2101/08* (2013.01); *C07C 2101/14* (2013.01)

(58) Field of Classification Search
CPC ...................................................... C07D 333/24
USPC ............................................................ 549/79
See application file for complete search history.

(56) References Cited

U.S. PATENT DOCUMENTS

| | | | |
|---|---|---|---|
| 5,434,292 | A | 7/1995 | Saita et al. |
| 8,431,614 | B2 | 4/2013 | Mizushima et al. |
| 8,778,298 | B2 | 7/2014 | Takashima et al. |

FOREIGN PATENT DOCUMENTS

| | | |
|---|---|---|
| EP | 2 402 305 A1 | 1/2012 |
| EP | 2 463 263 A1 | 6/2012 |
| JP | 2010-195727 A | 9/2010 |
| WO | WO 93/02999 A1 | 2/1993 |
| WO | WO 2010/098251 A1 | 9/2010 |
| WO | WO 2011/016376 A1 | 2/2011 |

OTHER PUBLICATIONS

King, Med. Chem., Principle and Practice (1994), pp. 206-208.*
Corresponding International Search Report dated Mar. 12, 2013 with English Translation (five (5) pages).
Japanese-language Written Opinion dated Mar. 12, 2013(PCT/ISA/237) (four (4) pages).

(Continued)

*Primary Examiner* — Taofiq A Solola
(74) *Attorney, Agent, or Firm* — Crowell & Moring LLP

(57) ABSTRACT

Provided are novel 2-fluorophenyl propionic acid derivatives which have excellent anti-inflammatory/analgesic effects while avoiding side effects such as gastrointestinal disorders, namely 2-fluorophenyl propionic acid derivatives represented by the formula (I) below or pharmaceutically acceptable salts thereof,

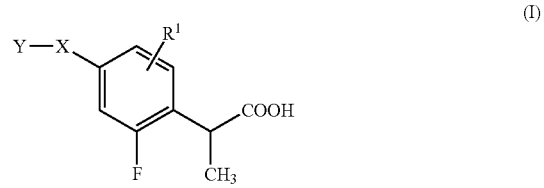

(I)

[wherein, $R^1$ represents a hydrogen atom, a halogen atom, or a substituted or unsubstituted phenyl group, X represents —$CH_2$—, —NH—, —O—, or —S—, and Y specifically represents group (II)

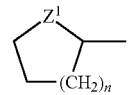

(wherein, $Z^1$ represents —CO—, —CH(OH)—, or —$CH_2$—, and n represents an integer of 1 or 2.)]

14 Claims, 2 Drawing Sheets

(56) References Cited

OTHER PUBLICATIONS

Naoki Yamakawa et al., "Properties and Synthesis of 2-{2-Fluoro (or Bromo)-4-[(2-oxocyclopentyl)methyl]phenyl}propanoic Acid: Nonsteroidal Anti-inflammatory Drugs with Low Membrane Permeabilizing and Gastric Lesion-Producing Activities", Journal of Medicinal Chemistry, 2010, vol. 53, No. 21, pp. 7879-7882.

Naoki Yamakawa et al., "Synthesis and Biological Evaluation of Loxoprofen Derivatives", Bioorganic & Medicinal Chemistry, 2011, vol. 19, No. 11, pp. 3299-3311.

Naoki Yamakawa et al., "Synthesis and Biological Evaluation of Derivatives of 2-{2-Fluoro-4-[(2-oxocyclopentyl)methyl]phenyl}propanoic Acid: Nonsteroidal Anti-Inflammatory Drugs with Low Gastric Ulcerogenic Activity", Journal of Medicinal Chemistry, 2012, vol. 55, No. 11, pp. 5143-5150.

Garret A. Fitzgerald et al., "The Coxibs, Selective Inhibitors of Cyclooxygenase-2", N. Engl. J. of Med., www.nejm.org, Aug. 9, 2001, vol. 345, No. 6, pp. 433-442.

Debabrata Mukherjee et al., "Risk of Cardiovascular Events with Selective COX-2 Inhibitors", http://jama.jamanetwork.com/ American Medical Association, 2001, vol. 286, No. 8, pp. 954-959.

Debabrata Mukherjee, "Selective Cyclooxygenase-2 (COX-2) Inhibitors and Potential Risk of Cardiovascular Events", Biochemical Pharmacology, Elsevier, 2002, vol. 63, pp. 817-821.

Wataru Tomisato et al., "Role of Direct Cytotoxic Effects of NSAIDs in the Induction of Gastric Lesions", Biochemical Pharmacology, Elsevier, 2004, vol. 67, pp. 575-585.

Wataru Tomisato et al., "Membrane Permeabilization by Non-Steroidal Anti-Inflammatory Drugs", Science Direct, BBRC, Elsevier, 2004, vol. 323, pp. 1032-1039.

\* cited by examiner

A

B

2-FLUOROPHENYL PROPIONIC ACID DERIVATIVES

TECHNICAL FIELD

The present invention relates to novel 2-fluorophenyl propionic acid derivatives having an excellent anti-inflammatory effect and high safety. More particularly, the present invention relates to 2-fluorophenyl propionic acid derivatives having no side effect such as gastrointestinal disorders and being useful as pharmaceuticals.

BACKGROUND ART

Non-steroidal anti-inflammatory drugs (NSAIDs), which have been clinically widely used as pharmaceuticals having excellent analgesic, anti-inflammatory, and antipyretic effects, account for about 5% of all prescription drugs in Japan.

NSAIDs suppress generation of prostaglandins (PGs), for example, $PGE_2$, by the inhibitory action on cyclooxygenase (COX) activity and thus exhibit an excellent anti-inflammatory effect. NSAIDs, however, have strong gastrointestinal side effects.

Since $PGE_2$ has a strong protective action on the gastrointestinal mucosa, it has been considered that the gastrointestinal side effect of NSAIDs is based on the inhibitory action on COX activity.

Of COX subtypes, particularly COX-1 and COX-2 are main enzymes involved in the inflammation activity of COX in the gastrointestinal mucosa or tissues. Because of this, selective inhibitors of COX-2 activity can reduce side effects in the stomach and duodenal site (Non-Patent Literature 1).

However, these selective inhibitors of COX-2 activity have been recently reported to impose a potential risk of thrombosis on the cardiovascular system, such as myocardial infarction (Non-Patent Literatures 2 and 3).

Since prostacyclins having strong platelet aggregation inhibitory and vasodepressor effects are mainly produced by selective inhibitors of COX-2 activity, from the above viewpoint, development of NSAIDs having no gastrointestinal side effects and being independent of selective inhibitors of COX-2 activity has been needed under present circumstances.

The present inventors have showed that apoptosis by NSAIDs independent of COX was found in NSAID-induced gastric tissues and direct cytotoxicity of NSAIDs is based on the gastric mucosa permeability (Non-Patent Literatures 4 and 5). As a result, the present inventors have proposed that NSAIDs with low gastric mucosa permeability are independent of selective COX-2 inhibitory activity and safe to the gastric tissues.

Loxoprofen (1) described below has been widely clinically used as a NSAID independent of selective inhibitory action on COX-2 activity and been safer than indomethacin, which has been used as a common NSAID. Loxoprofen (1) is accordingly a standard anti-inflammatory drug in Japan.

Loxoprofen (1), so-called prodrug, is absorbed in a gastrointestinal tract site and then converted to its active form trans-alcohol in vivo. Loxoprofen (1) has lower mucosa permeability activity than other NSAIDs and can be also called a leading compound for searching a compound that is less involved in ulceration in the gastrointestinal mucosa.

According to such a point of view, the present inventors have provided 2-fluoroloxoprofen (2) described below in which a fluorine atom is introduced to the 2-position of loxoprofen (1). The present inventors have confirmed that this 2-fluoroloxoprofen has a low ulceration action and to have the same anti-inflammatory effect as loxoprofen. The patent application on compounds including 2-fluoroloxoprofen has already been filed (Patent Literature 1).

[Chemical Formula 1]

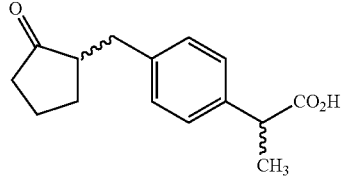

Loxoprofen (1)

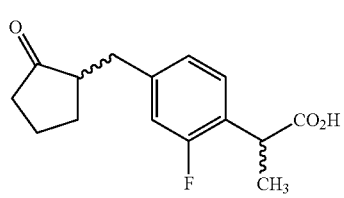

2-Fluoroloxoprofen (2)

The present inventors have further studied on 2-fluoroloxoprofen derivatives and as a result, have successfully synthesized compounds which have more excellent anti-inflammatory and analgesic effects while avoiding side effects such as gastrointestinal disorders caused by ulcerogenesis, to thereby complete the present invention.

PRIOR ART LIST

Patent Document

Patent Literature 1: Japanese Patent Application Laid-Open No. 2010-195727

Non-Patent Document

Non-Patent Literature 1: N. Engl. J. Med., 345, pp 433-442 (2001)
Non-Patent Literature 2: JAMA, 286, pp 954-959 (2001)
Non-Patent Literature 3: Biochem. Pharmacol., 63, pp 817-821 (2001)
Non-Patent Literature 4: Biochem. Pharmacol., 67, pp 575-585 (2004)
Non-Patent Literature 5: Biochem. Biophys. Res. Commun., 323, pp 1032-1039 (2004)

DISCLOSURE OF INVENTION

Problem to be Solved by the Invention

Accordingly, it is an object of the present invention to provide novel 2-fluoro-loxoprofen derivatives which have excellent anti-inflammatory/analgesic effects while avoiding side effects such as gastrointestinal disorders, specifically to provide 2-fluorophenyl propionic acid derivatives.

Means for Solving the Problem

The present invention to solve the aforementioned problems is a 2-fluorophenyl propionic acid derivative represented by the following formula (I) or a pharmaceutically acceptable salt thereof:

[Chemical Formula 2]

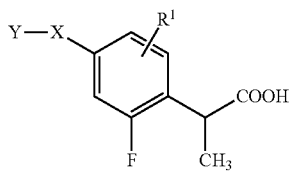
(I)

[wherein,
$R^1$ represents a hydrogen atom, a halogen atom, or a substituted or unsubstituted phenyl group,
X represents —$CH_2$—, —NH—, —O—, or —S—, and
Y represents
group (1):

[Chemical Formula 3]

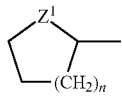

(wherein, $Z^1$ represents —CO—, —CH(OH)—, or —$CH_2$—, and n represents an integer of 1 or 2),
group (2):

[Chemical Formula 4]

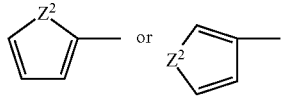

(wherein, $Z^2$ represents an oxygen atom or a sulfur atom), or group (3):

[Chemcial Formula 5]

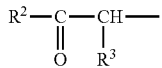

(wherein, $R^2$ and $R^3$, which are the same or different, represent a lower alkyl group), with the exception of the case where, simultaneously, $R^1$ is a hydrogen atom, X is —$CH_2$—, $Z^1$ is —CO— or —CH(OH)—, and n is 1.

Accordingly, a specific aspect of the present invention is the 2-fluorophenyl propionic acid derivative or the pharmaceutically acceptable salt thereof, wherein the formula (I) is represented by the formula (I-a):

[Chemical Formula 6]

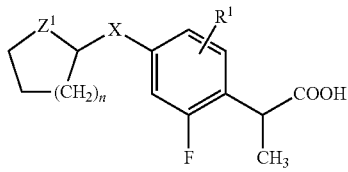
(I-a)

(wherein, $R^1$, X, $Z^1$, and n have the same definitions as described above).

Another specific aspect of the present invention is the 2-fluorophenyl propionic acid derivative or the pharmaceutically acceptable salt thereof, wherein the formula (I) is represented by the formula (I-b):

[Chemical Formula 7]

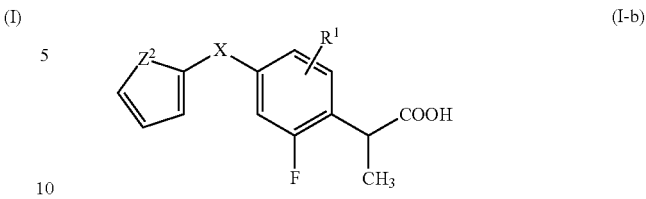
(I-b)

(wherein, $R^1$, X, and $Z^2$ have the same definitions as described above).

Yet another specific aspect of the present invention is the 2-fluorophenyl propionic acid derivative or the pharmaceutically acceptable salt thereof, wherein the formula (I) is represented by the formula (I-c):

[Chemical Formula 8]

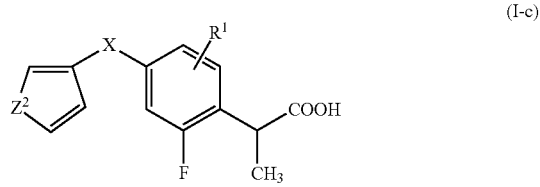
(I-c)

(wherein, $R^1$, X, and $Z^2$ have the same definitions as described above).

Still yet another specific aspect of the present invention is the 2-fluorophenyl propionic acid derivative or the pharmaceutically acceptable salt thereof, wherein the formula (I) is represented by the formula (I-d):

[Chemical Formula 9]

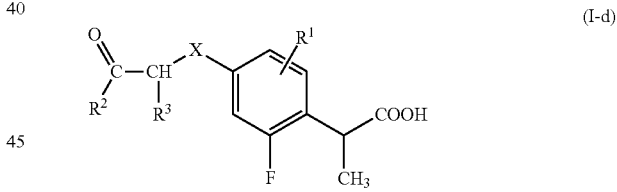
(I-d)

(wherein, $R^1$, $R^2$, $R^3$, and X have the same definitions as described above).

More specifically, the present invention is the 2-fluorophenyl propionic acid derivative or the pharmaceutically acceptable salt thereof, wherein the halogen atom of $R^1$ in the above formulas is selected from a chlorine atom, a bromine atom, a fluorine atom, and an iodine atom, or wherein the substituent of $R^1$ in the substituted phenyl group in the formulas is a halogen atom or a hydroxyl group.

Effect of the Invention

The 2-fluorophenyl propionic acid derivatives provided by the present invention are novel compounds which have been hitherto unknown and which have no side effects such as gastrointestinal disorders, which are caused by conventional acid NSAIDs, and further have anti-inflammatory and analgesic effects stronger than those of loxoprofen, which has been clinically used. The 2-fluorophenyl propionic acid derivatives have a weak selective inhibitory action on COX-2 activity, and thus can avoid a risk to cardiovascular system, such as myocardial infarction.

Accordingly, because of the wide margin of safety, the 2-fluorophenyl propionic acid derivatives are very effective in terms of safety for use in human.

BRIEF DESCRIPTION OF DRAWINGS

FIG. 2A shows the inhibition rate at 3 hours after administration and FIG. 2B shows the inhibition rate at 6 hours after administration.

MODES FOR CARRYING OUT THE INVENTION

Figure 1:
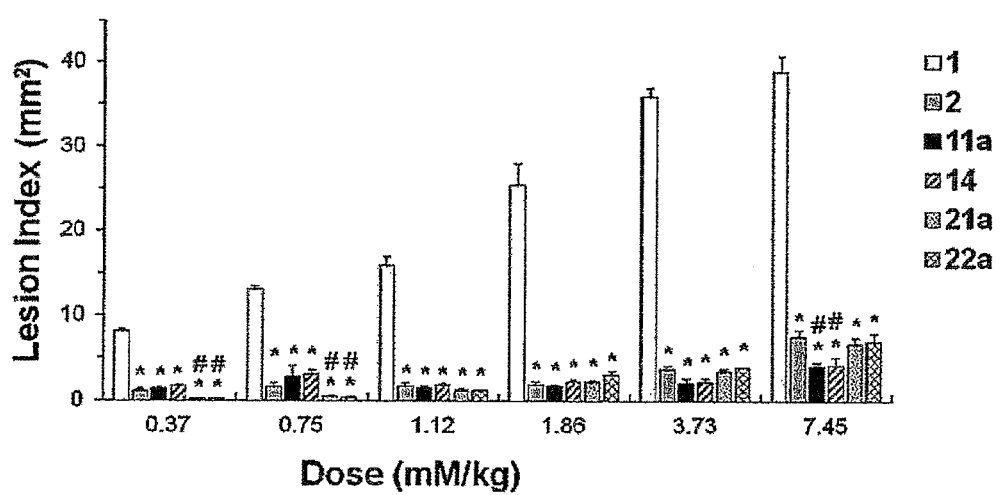
FIG. 1 is a figure illustrating the result of [A: Gastric Ulceration] in Test Example 2.

As described above, a basic aspect of the present invention is the 2-fluoro-propionic acid derivative represented by the following formula (I), specifically, the formula (I-a), (I-b), (I-c), or (I-d) below, or the pharmaceutically acceptable salt thereof:

[Chemical Formula 10]

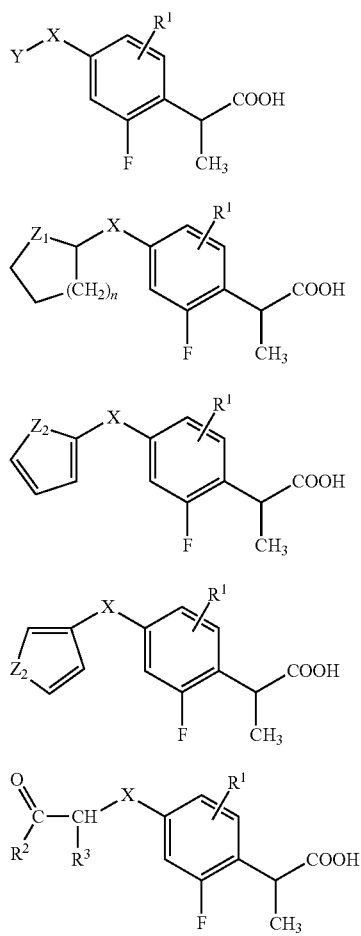

(wherein $R^1$, $R^2$, $R^3$, X, Y, $Z^1$, $Z^2$, and n have the same definitions as described above).

In this specification, the halogen atom in the substituent $R^1$ refers to a halogen atom selected from a chlorine atom, a bromine atom, a fluorine atom, and an iodine atom.

A lower alkyl group which is the substituent represented by the substituent $R^1$ in the substituted phenyl group refers to a substituted or unsubstituted alkyl group having about 1 to 6 carbon atoms, and specifically means to include a methyl group, an ethyl group, a propyl group, an isopropyl group, a butyl group, an isobutyl group, a sec-butyl group, a tert-butyl group, a pentyl group, an isopentyl group, and a hexyl group.

The substituents in these lower alkyl groups include a hydroxyl group, an amino group, and a nitro group.

Although the position and the number of the substituent(s) in the substituted phenyl group are not particularly limited, the substituted phenyl group is preferably a mono-substituted phenyl group and the substituent is preferably located at the ortho position or the meta position.

Furthermore, the lower alkyl groups represented by $R^2$ and $R^3$ refer to lower alkyl groups having 1 to 6 carbon atoms, and specifically means to include a methyl group, an ethyl group, a propyl group, an isopropyl group, a butyl group, an isobutyl group, a sec-butyl group, a tert-butyl group, a pentyl group, an isopentyl group, and a hexyl group.

Specific novel loxoprofen derivatives provided by the present invention include compounds of the following types (Type-A, Type-B, and Type-C), and specific compounds include compounds described below in Examples.

[Chemical Formula 11]

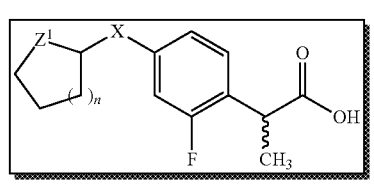

Type-A

X: NH, O, S
$Z^1$: C=O, CH(OH), $CH_2$
n: 1-2

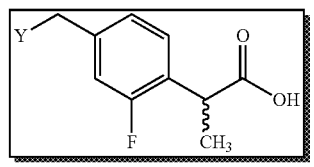

Type-B

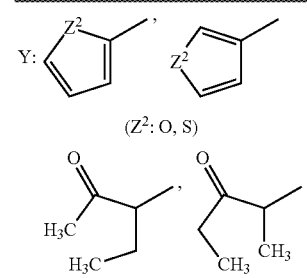

Y:

($Z^2$: O, S)

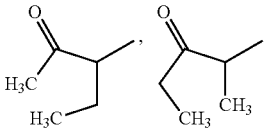

-continued

Type-C

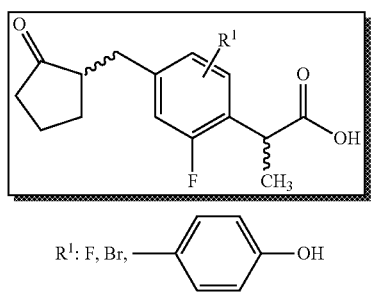

$R^1$: F, Br, —⟨C₆H₄⟩—OH

In the above formulas (I), (I-a), (I-b), (I-c), and (I-d), the methyl group of the phenylpropionic acid moiety can have an α-configuration or a β-configuration. In the present invention, the configuration of the methyl group may be any of these or a mixture of these.

Furthermore, when the ring in the formula (I-a) has the substituent at the 2-position, the 1-position and the 2-position can take a cis- and trans-configuration. The present invention may include 1,2-cis isomer, 1,2-trans isomer, and a mixture of these diastereomers.

The novel 2-fluorophenyl propionic acid derivatives provided by the present invention can be specifically produced in the following manner.

It can be understood that a production process described below is a specific production process so that the production process is not limited thereto, and the 2-fluorophenyl propionic acid derivatives can be produced by various methods with reference to a general chemistry textbook.

In the production of the 2-fluorophenyl propionic acid derivatives provided by the present invention, compounds (7) to (9) described below in Production Schemes are basic production intermediates and can be synthesized, for example, according to Production Scheme 1 represented by the following chemical equation.

[Production Scheme 1]

[Chemical Formula 12]

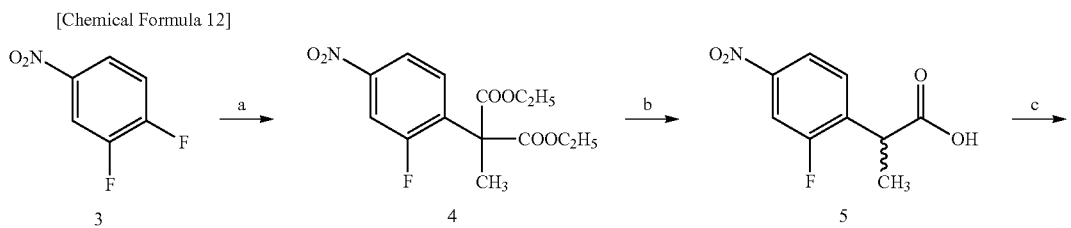

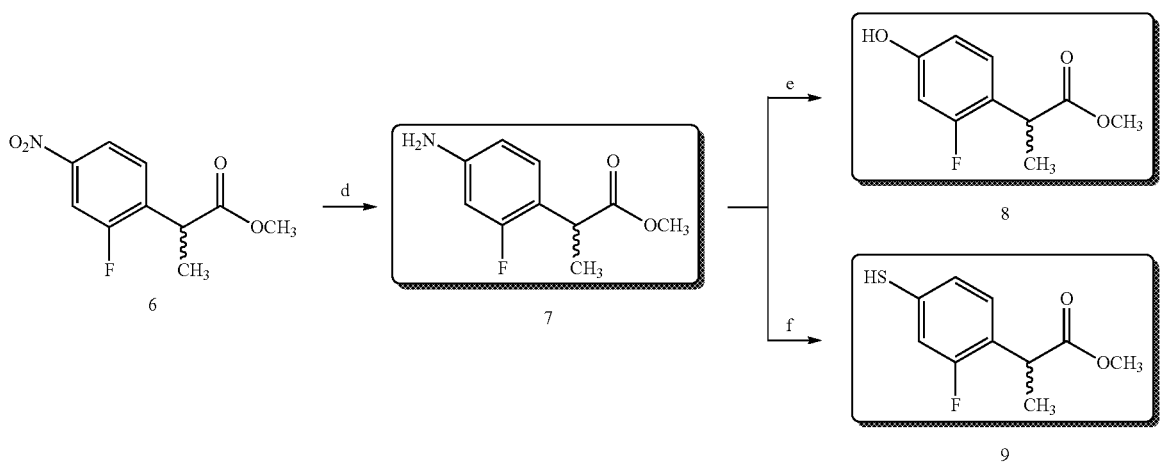

Reagents and conditions:
(a) Diethyl methylmalonate, NaOH, DMF; (b) conc. $H_2SO_4$, AcOH, reflux; (c) MeOH, conc. HCl, reflux;
(d) $H_2$, 10% Pd/C, MeOH; (e) i) 6M $H_2SO_4$, $NaNO_2$, $H_2O$, ii) 3M $H_2SO_4$, reflux, iii) MeOH, conc. HCl, reflux; (f) i) conc. HCl, $NaNO_2$, $H_2O$, ii) EtOCSSK, $H_2O$.

In the chemical equation, Arabic numerals represent specific compound numbers (the same is applied to Production Schemes below.)

In the chemical equation, (a) to (f) indicate reaction reagents/reaction conditions for preparing compounds of interest in Production Scheme above by way of a preferred specific example. The reaction reagents/reaction conditions are not limited to these.

It should be understood that the reaction procedure conditions (time, temperature, etc.), reaction treatments, and the like can be carried out according to a method described in a general chemistry textbook.

The specific conditions thereof will be illustrated in Examples described below.

Specifically, first, commercially available 1,2-difluoro-4-nitrotoluene (3) is converted into diethyl 2-(2-fluoro-4-nitrophenyl)-2-methylmalonate represented by the formula (4) by the reaction with diethyl methylmalonate in the presence of an alkali in a suitable solvent, for example, dimethylformamide (hereafter, referred to as "DMF".)

Next, the obtained diester of the formula (4) is converted into nitrophenyl propionic acid of the formula (5) through acid hydrolysis and decarboxylation.

This conversion can be carried out, for example, by reflux in an acetic acid solution in the presence of concentrated sulfuric acid as an acid.

The obtained nitrophenyl propionic acid of the formula (5) is then subjected to esterification by a conventional method to give nitrophenyl propionate of the formula (6). This esterification can be carried out, for example, by the reflux reaction with an acid catalyst in a lower alcohol. The use of methanol as a lower alcohol can produce a methyl ester, and the use of ethanol can produce an ethyl ester.

The nitro group of the nitrophenyl propionate obtained above is reduced to provide 4-aminophenyl propionate (7).

This reduction reaction can be carried out, for example, by catalytic reduction in the presence of an alcohol solvent using palladium-carbon to absorb a calculated amount of hydrogen.

The obtained 4-aminophenyl propionate of the formula (7) is an intermediate to prepare the 2-fluorophenyl propionic acid derivative of the formula (I) of the present invention where "X" is a nitrogen atom.

On the other hand, the 2-fluorophenyl propionic acid derivative of the formula (I) of the present invention where "X" is an oxygen atom can be obtained by diazotization of the amino group of the compound of the formula (7) with sulfuric acid/sodium nitrite/water and subsequent alcoholysis with an acid catalyst to give 4-hydroxyphenyl propionate of represented by the formula (8).

The 2-fluorophenyl propionic acid derivative of the formula (I) of the present invention where "X" is a sulfur atom can be obtained by diazotization of the amino group of the compound of the formula (7) with sulfuric acid/sodium nitrite/water and subsequent treatment with potassium ethylxanthate (EtOCSSK) to give 4-mercaptophenyl propionate represented by the formula (9).

The production intermediates (7) to (9) of the 2-fluoropropionic acid derivative provided by the present invention are prepared according to Production Scheme above. These compounds are provided as starting compounds to produce the 2-fluorophenyl propionic acid derivative of the formula (I-a), which is the formula (I) of the present invention, specifically according to Production Scheme below.

[ProductionScheme2]

[Chemical Formula 13]

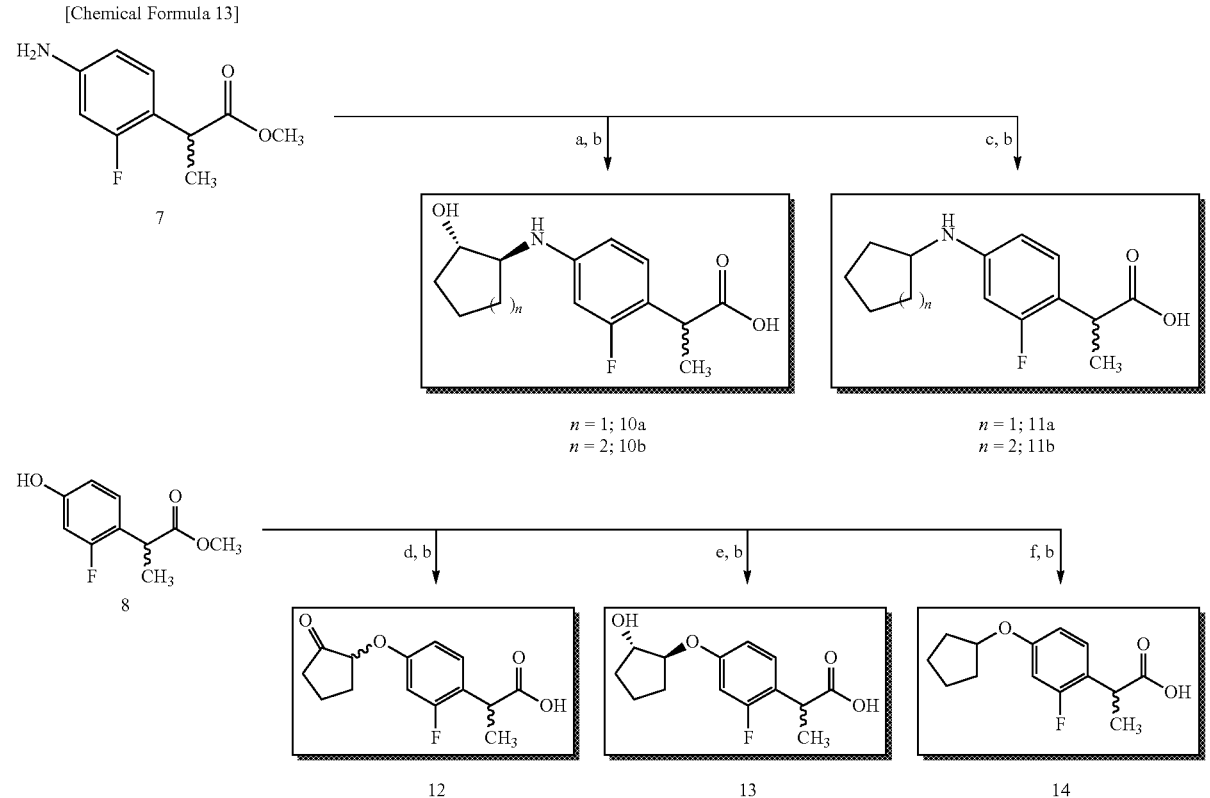

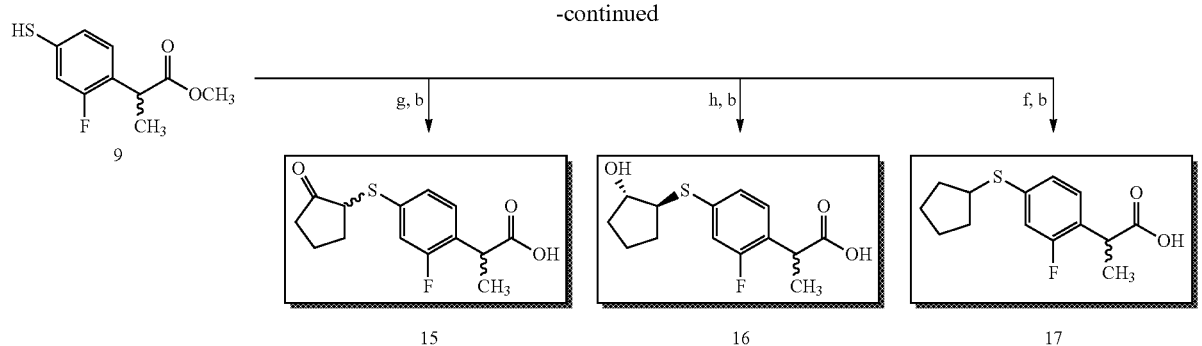

Reagents and conditions:
(a) Cyclopenteneoxide or Cyclohexaneoxide, LiBr, CH₂Cl₂; (b) NaOH, H₂O, MeOH, reflux; (c) Cyclopentanone or Cyclohexanone, NaBH₃CN, AcOH,MeOH; (d) Chloroycyclopentanone, K₂CO₃, DMF; (e) Cyclopenteneoxide, NaH, DMF; (f) Bromocyclopentane, K₂CO₃, DMF; (g) Cyclopentanone, NBS, CH₂Cl₂; (h) 1,2-Epoxycyclopentene, Borax, CH₂Cl₂.

In the chemical equation, (a) to (h) indicate reaction reagents/reaction conditions for preparing the compounds of interest in Production Scheme above by way of a preferred specific example. The reaction reagents/reaction conditions are not limited to these.

In the description of, for example, "a, b" and "c, b" in Reaction Scheme, "a, b" means reaction/treatment (a) followed by reaction/treatment (b), and "c, b" means reaction/treatment (c) followed by reaction/treatment (b).

In this case, it should be understood that the reaction procedure conditions (time, temperature, etc.), reaction treatments, and the like can be carried out according to a method described in a general chemistry textbook.

Specifically, the above reaction reagents and reaction conditions are used with 4-aminophenyl propionate of the formula (7) as a starting material to prepare compounds of the respective formulas (10a), (10b), (11a), and (11b) where "X" is a nitrogen atom in the formula (I-a).

In addition, 4-hydroxyphenyl propionate of the formula (8) is provided as a starting material to prepare compounds of the respective formulas (12), (13), and (14) where "X" is an oxygen atom in the formula (I-a).

Moreover, 4-mercaptophenyl propionate of the formula (9) is provided as a starting material to prepare compounds of the respective formulas (15), (16), and (17) where "X" is a sulfur atom in the formula (I-a).

It is noted that the actual reactions, the treatments thereof, and the like can be carried out on the basis of a method described in a general chemistry textbook and the details thereof will be illustrated in Examples below.

In addition, the compounds of the formulas (I-b), (I-c), and (I-d) as other compounds of the formula (I) of the present invention can be prepared by using 4-hydroxyphenyl propionate represented by the formula (8) as a starting material according to the chemical equation in Production Scheme below.

[Production Scheme 3]

[Chemical Formula 14]

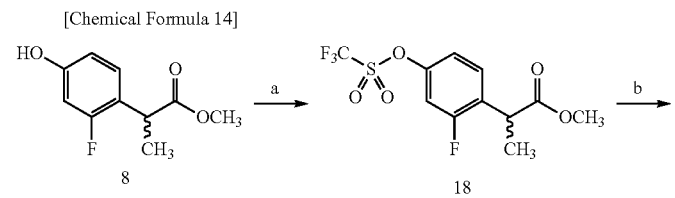

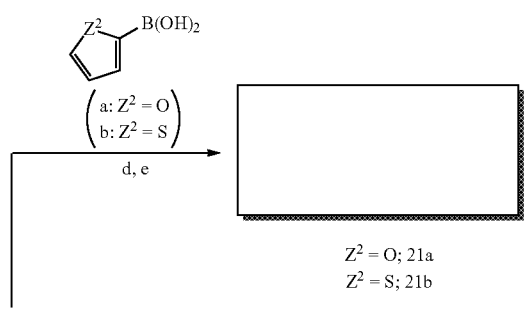

$Z^2$ = O; 21a
$Z^2$ = S; 21b

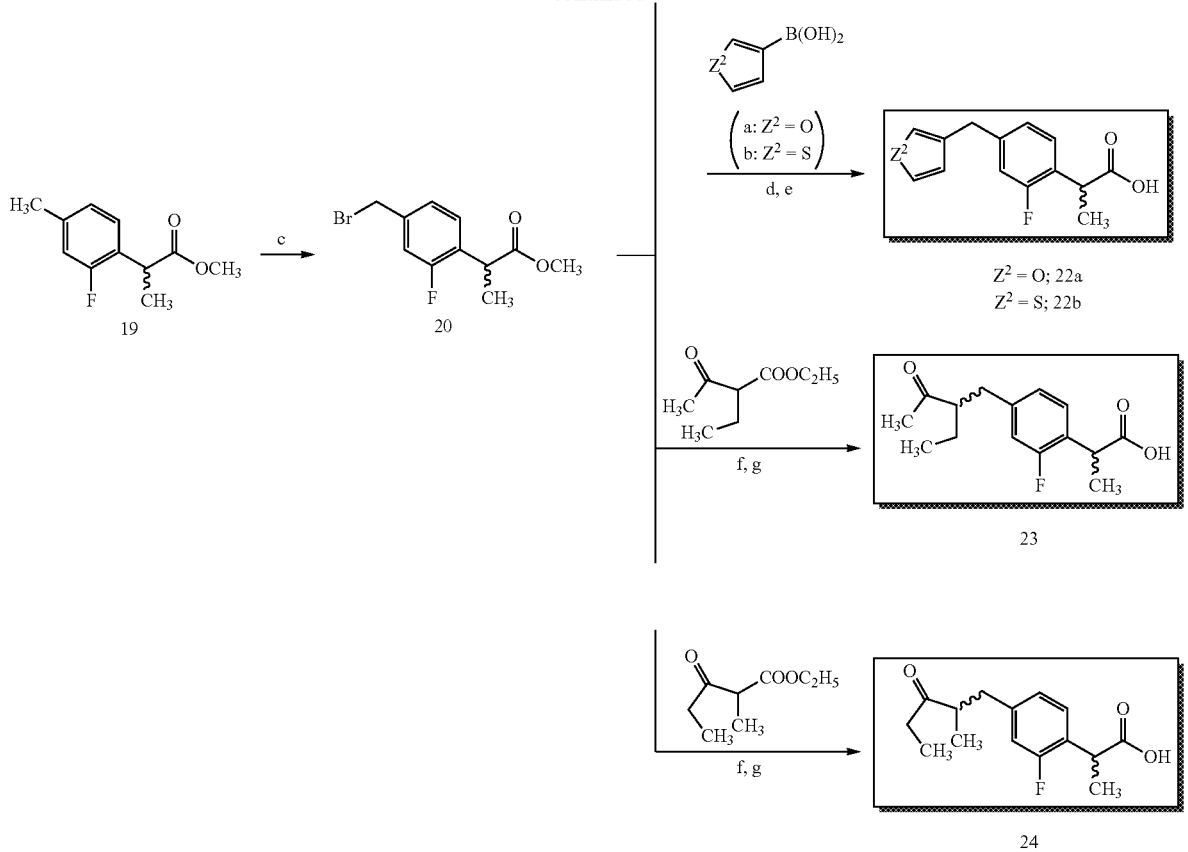

Reagents and conditions:
(a) (CF$_3$SO$_2$)$_2$O, Et$_3$N, CH$_2$Cl$_2$; (b) Zn(CH$_3$)$_2$, Pd(dppe)Cl$_2$, 1,4-Dioxane, reflux; (c) NBS, AIBN, CCl$_4$, reflux; (d) 3M Na$_2$CO$_3$, trans-PdBr(N-Succ)(PPh$_3$)$_2$, THF, reflux; (e) KOH, H$_2$O, EtOH, reflux; (f) dry Na$_2$CO$_3$, dry Acetone, reflux; (g) conc. HCl, AcOH, reflux.

In the chemical equation, (a) to (g) indicate reaction reagents/reaction conditions for preparing the compounds of interest in Production Scheme above by way of a preferred specific example. The reaction reagents/reaction conditions are not limited to these.

In the description of, for example, "d, e" and "f, g" in Reaction Scheme, "d, e" means reaction/treatment (d) followed by reaction/treatment (e), and "f, g" means reaction/treatment (f) followed by reaction/treatment (g).

In this case, it should be understood that the reaction procedure conditions (time, temperature, etc.), reaction treatments, and the like can be carried out according to a method described in a general chemistry textbook.

Specifically, the 4-hydroxyphenyl propionic acid derivative represented by the formula (8) produced according to Production Scheme 1 described above is treated with, for example, trifluoromethanesulfonic anhydride ((CF$_3$SO$_2$)$_2$O) in the presence of triethylamine as a base in a dichloromethane solvent to give the compound of the formula (18). Next, the compound of the formula (18) is reacted with dimethyl zinc (Zn(CH$_3$)$_2$) in 1,4-dioxane using Pd(dppe)Cl$_2$ ([1,2-bis(diphenylphosphine)ethane]dichloropalladium) as a catalyst to give a 4-methylphenyl propionic acid derivative represented by the formula (19).

Next, the compound of the formula (19) is treated with NBS (N-bromosuccinimid) in the presence of AIBN (azobisisobutyronitrile) to provide 4-bromomethylphenyl propionate, which is an intermediate represented by the formula (20). The 4-bromomethylphenyl propionate is subjected to Suzuki-Miyamura cross-coupling reaction with respective boronate derivatives to provide compounds of the formulas (21-a, b) and (22-a, b), which are the corresponding compounds of interest in the present invention.

In addition, the 4-bromomethylphenyl propionate, which is the intermediate of the formula (20), is reacted with corresponding acetoacetic acid derivatives to provide compounds represented by the formulas (23) and (24), which are other compounds of interest.

The 2-fluorophenyl propionic acid derivative of the present invention belonging to the group of type C described above can be prepared, for example, according to the chemical equation in Production Schemes 4 below.

[Production Scheme 4]

[Chemical Formula 15]

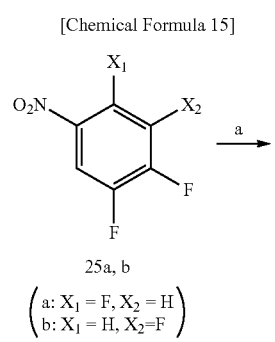

$$\begin{pmatrix} a: X_1 = F, X_2 = H \\ b: X_1 = H, X_2 = F \end{pmatrix}$$

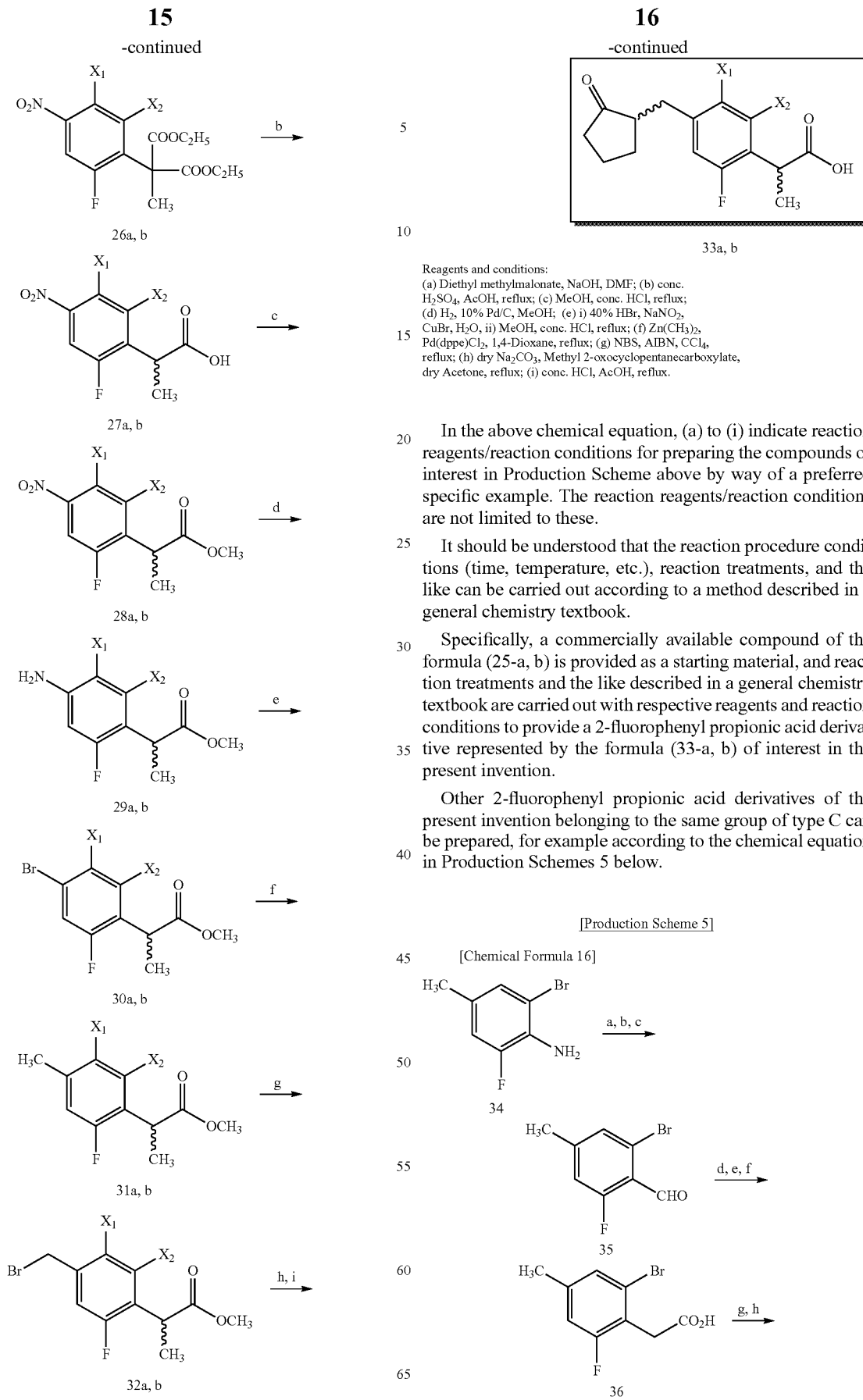

Reagents and conditions:
(a) Diethyl methylmalonate, NaOH, DMF; (b) conc. $H_2SO_4$, AcOH, reflux; (c) MeOH, conc. HCl, reflux; (d) $H_2$, 10% Pd/C, MeOH; (e) i) 40% HBr, $NaNO_2$, CuBr, $H_2O$, ii) MeOH, conc. HCl, reflux; (f) $Zn(CH_3)_2$, $Pd(dppe)Cl_2$, 1,4-Dioxane, reflux; (g) NBS, AIBN, $CCl_4$, reflux; (h) dry $Na_2CO_3$, Methyl 2-oxocyclopentanecarboxylate, dry Acetone, reflux; (i) conc. HCl, AcOH, reflux.

In the above chemical equation, (a) to (i) indicate reaction reagents/reaction conditions for preparing the compounds of interest in Production Scheme above by way of a preferred specific example. The reaction reagents/reaction conditions are not limited to these.

It should be understood that the reaction procedure conditions (time, temperature, etc.), reaction treatments, and the like can be carried out according to a method described in a general chemistry textbook.

Specifically, a commercially available compound of the formula (25-a, b) is provided as a starting material, and reaction treatments and the like described in a general chemistry textbook are carried out with respective reagents and reaction conditions to provide a 2-fluorophenyl propionic acid derivative represented by the formula (33-a, b) of interest in the present invention.

Other 2-fluorophenyl propionic acid derivatives of the present invention belonging to the same group of type C can be prepared, for example according to the chemical equation in Production Schemes 5 below.

-continued

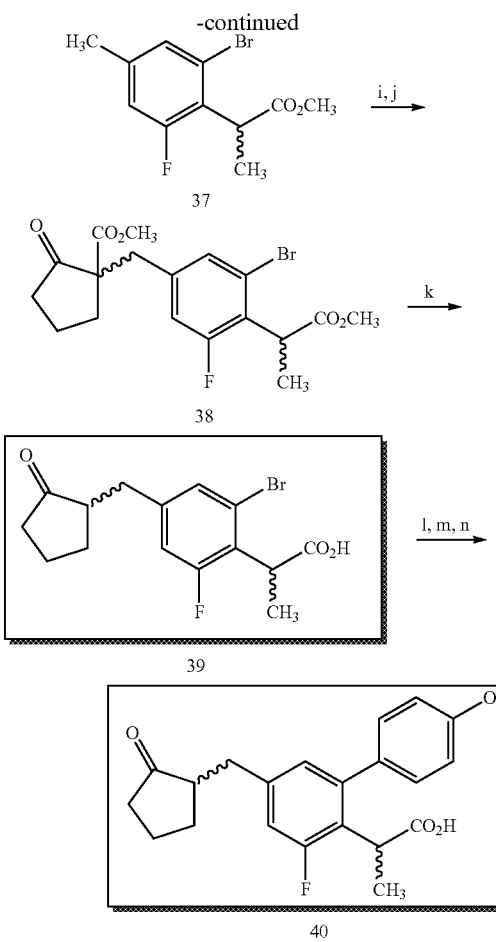

Reagents and conditions:
(a) 3M HCl aq., NaNO$_2$, CuSO$_4$, Na$_2$SO$_3$, AcONa, H$_2$O, 0° C.; (b) NH$_2$OH•HCl, (HCHO)$_n$, AcONa, H$_2$O; (c) conc. HCl, reflux; (d) MeOCH$_2$P(Ph$_3$)Cl, C$_6$H$_{18}$KNSi$_2$, Toulene; (e) 3M, HCl aq., Acetone, reflux; (f) PFC (2.0 mol%), H$_5$IO$_6$, Acetonitrile; (g) conc. HCl, CH$_3$OH, reflux; (h) 2.0M LDA, CH$_3$I, dry THF, -78° C. to -40° C.; (i) NBS, AIBN, CCl$_4$, reflux; (j) dry NA$_2$CO$_3$, Methyl 2-oxocyclopentanecarboxylate, dry Acetone, reflux; (k) conc. HCl, AcOH, reflux. (l) 4-DMAP, EDC, CH$_3$OH;

(m) HO—⟨benzene⟩—B(OH)$_2$, Pd(PPh$_3$)$_4$, Na$_2$CO$_3$, THF, reflux; (n) KOH, C$_2$H$_5$OH, H$_2$O, reflux.

In the above chemical equation, (a) to (n) indicate reaction reagents/reaction conditions for preparing the compounds of interest in Production Scheme above by way of a preferred specific example. The reaction reagents/reaction conditions are not limited to these.

It should be understood that the reaction procedure conditions (time, temperature, etc.), reaction treatments, and the like can be carried out according to a method described in a general chemistry textbook.

Specifically, the amino group of a commercially available compound represented by the formula (34) is diazotized to the formyl group to provide a compound represented by the formula (35). Next, the compound of the formula (35) is subjected to Wittig reaction, which increases the number of carbon atoms, and oxidation with pyridinium fluorochromate (PFC) to give a phenylacetic acid derivative represented by the formula (36).

The obtained phenylacetic acid of the formula (36) is brominated in the α-position, and the bromine atom is substituted by a methyl group to give a compound represented by the formula (37). The compound of the formula (37) is then treated in the same manner as in the conversion of the formula (19) to the formula (22) in Production Scheme 3 to give a compound represented by the formula (38). The compound of the formula (38) is decarboxylated to give a compound of the formula (39), which is a 2-fluorophenyl propionic acid derivative of interest in the present invention.

The compound of the formula (39) is further subjected to Suzuki-Miyamura cross-coupling reaction to give a compound represented by the formula (40), which is the corresponding compound of interest in the present invention.

The 2-fluorophenyl propionic acid derivatives of the present invention provided by the above production processes can be used as the free carboxylic acid itself or as the pharmaceutically acceptable salt thereof.

The pharmaceutically acceptable salts include alkali metal salts such as a sodium salt and a potassium salt, and an ammonium salt.

When the 2-fluorophenyl propionic acid derivative provided by the present invention or the pharmaceutically acceptable salt thereof is administrated as a pharmaceutical composition, for example, an active ingredient which is the derivative or the pharmaceutically acceptable salt thereof can be orally or parenterally administrated singly or in combination with a conventional vehicle, as a suitable dosage form such as a capsule, a tablet, and an injection. Specifically, for example, a capsule can be prepared by: mixing the 2-fluorophenyl propionic acid derivative or the salt thereof with a vehicle such as lactose, starch or a derivative thereof, or a cellulose derivative; and filling a gelatin capsule with the mixture.

A tablet can be prepared by: adding, to the 2-fluorophenyl propionic acid derivative or the salt thereof, water and a binder such as carboxymethyl cellulose sodium, alginic acid, or gum arabic in addition to the above vehicle, followed by kneading and optional granulation; further adding a lubricant such as talc or stearic acid to the obtained mixture; and forming tablets using an ordinary compression tableting machine.

Furthermore, for parenteral administration by injection, the 2-fluorophenyl propionic acid derivative or the salt thereof is dissolved together with a solubilizer in sterile distilled water or sterile physiological saline, and the obtained solution is enclosed in an ampule to provide an injection preparation. A stabilizer, a buffer substance, and the like may be optionally contained in the injection preparation. These parenteral preparations can be administrated by intravenous injection or by intravenous drip.

The dose of the 2-fluorophenyl propionic acid derivative provided by the present invention cannot be restricted only by several factors such as, for example, symptoms, severity, and age of patients to be treated, and presence of complication.

The dose also depends on administration route, dosage form, frequency of administration, and the like. In general, the dose for oral administration is usually within the range of from 0.1 to 1000 mg/day/person, preferably from 1 to 500 mg/day/person based on the active ingredient, and the dose for parenteral administration can be appropriately selected within the range of from about 1/100 to 1/2 of the dose for oral administration. It should be noted that these doses can be appropriately changed depending on patient age, symptoms, and the like.

EXAMPLES

While the present invention will be described below in more detail on the basis of Production Examples, Examples, and Test Examples, the scope of the present invention is not limited to these examples.

Production Example 1

Production of Starting Compounds (7), (8), and (9)/Production of Intermediate Compounds [Intermediates in Reaction Scheme 1]

(a) Production of diethyl 2-(2-fluoro-4-nitrophenyl)-2-methylmalonate (4)

Commercially available compound (3), 3.0 mL (27 mmol), was dissolved in DMF (3 mL), and diethyl methylmalonate (3.9 mL, 22 mmol) and sodium hydroxide (0.98 g, 24.5 mmol) were added thereto and stirred at room temperature for 6 hours. After completion of the reaction, the reaction mixture was dried out, followed by extraction with dichloromethane. After drying (over sodium sulfate), the solvent was distilled off, and the residue was subjected to silica gel column chromatography and elution with an n-hexane/ethyl acetate mixture to give 7.12 g (84%) of compound (4) of interest as a pale brown oil.

(b) Production of 2-(2-fluoro-4-nitrophenyl)propionic acid (5)

Concentrated sulfuric acid (7.5 mL) was added to compound (4) obtained above (7.09 g, 22.6 mmol) in acetic acid (26 mL) and water (18 mL), and the obtained mixture was heated to reflux for 12 hours. After completion of the reaction, the mixture was cooled and concentrated under reduced pressure, and the residue was extracted with dichloromethane. The extract was washed with saturated saline and water and dried (over sodium sulfate). The solvent was then distilled off under reduced pressure to give 3.72 g (77%) of compound (5) of interest as clear reddish brown oil.

(c) Production of methyl 2-(2-fluoro-4-nitrophenyl)propionate (6)

Compound (5) obtained above was esterified by adding a catalytic amount of concentrated hydrochloric acid in methanol to give compound (6) of interest as a clear yellow oil at a yield of 93%.

(d) Production of methyl 2-(4-amino-2-fluorophenyl)propionate (7)

Compound (6) obtained above was allowed to absorb a calculated amount of hydrogen gas by catalytic reduction with 10% palladium-carbon as a catalyst in ethanol. After completion of the reaction, the catalyst was filtered off, and the filtrate was concentrated and dried out to give compound (7) of interest as clear orange oil at a yield of 93%.

(e) Production of methyl 2-(2-fluoro-4-hydroxyphenyl)propionate (8)

Compound (7) obtained above was diazotized followed by hydrolysis with a hydrochloric acid catalyst to give compound (8) of interest as clear orange oil at a yield of 54%.

(f) Production of methyl 2-(2-fluoro-4-mercaptophenyl)propionate (9)

Compound (7) obtained above was diazotized and subsequently treated with potassium ethylxanthate to give compound (9) of interest as colorless oil at a yield of 92%.

Example 1

Production of 2-[2-fluoro-4-((1S,2S)-2-hydroxycyclo-pentylamino)phenyl]propionic acid (10a)

To a solution of compound (7) (0.7 g, 3.6 mmol) obtained above in dichloromethane (3 mL), cyclopentene oxide (1.1 mL, 12.4 mmol) and lithium bromide (0.47 g, 5.4 mmol) were added and stirred at room temperature for 12 hours. After completion of the reaction, dichloromethane was added and the organic solvent was dried (over sodium sulfate) and distilled off under reduced pressure. The residue was subjected to silica gel column chromatography and elution with an n-hexane/ethyl acetate (3:1) solution followed by conventional hydrolysis to give 0.64 g (64%) of compound (10a) of interest as pale yellow oil.

Example 2

Production of 2-[2-fluoro-4-((1S,2S)-2-hydroxycyclo-hexylamino)phenyl]propionic acid (10b)

A solution of compound (7) obtained above (0.8 g, 4.0 mmol), cyclohexene oxide (1.3 mL, 13.1 mmol), and lithium bromide (0.37 g, 4.3 mmol) in dichloromethane (3 mL) was reacted and treated in the same manner as in Example 1. The obtained crude product was subjected to silica gel column chromatography and elution with an n-hexane/ethyl acetate (3:1) solution followed by conventional hydrolysis to give 0.97 g (81%) of compound (10b) of interest as brown solid.

Example 3

Production of 2-[4-(cyclopentylamino)-2-fluoro-phenyl]propionic acid (11a)

To a solution of 1.50 g (7.6 mmol) of compound (7) in a solvent mixture of 10 mL of methanol and 0.2 mL of acetic acid, 1.4 mL (15.2 mmol) of cyclopentanone and 0.96 g (15.2 mmol) of sodium cyanoborohydride ($NaBH_3CN$) were added. The obtained solution was stirred at room temperature for 12 hours. Next, the reaction mixture was dried under a vacuum and extracted with dichloromethane, followed by drying over anhydrous sodium sulfate and subsequent filtration. The filtrate was dried under a vacuum, and the residue was purified by silica gel chromatograph (n-hexane/ethyl acetate 3:2) to give a methyl ester of compound (11a). This compound was hydrolyzed with sodium hydroxide to give 1.09 g (yield 54%) of compound (11a) of interest as brown powder.

Example 4

Production of 2-[4-(cyclohexylamino)-2-fluoro-phenyl]propionic acid (11b)

A solution of compound (7) (1.50 g, 7.6 mmol), cyclohexanone (1.57 mL, 15.2 mmol), and $NaBH_3CN$ (0.96 g, 15.2 mmol) in methanol (10 mL) and acetic acid (0.2 mL) was allowed to undergo conventional reactions, followed by the same reactions and treatments as those in Example 3. The obtained crude product was subjected to silica gel column chromatography and elution with an n-hexane/ethyl acetate (4:1) solution followed by conventional hydrolysis to give 1.37 g (65%) of compound (11b) of interest as brown powder.

Example 5

Production of 2-[2-fluoro-4-(2-oxocyclopentyl-oxy) phenyl]propionic acid (12)

To a solution of compound (8) obtained above (0.87 g, 4.4 mmol) in dry DMF (8.7 mL), potassium carbonate and chlorocyclopentanone (0.53 mL, 5.3 mmol) were added, and the obtained mixture was heated to reflux for 3 hours. After the reaction, the mixture was filtered and the obtained filtrate was distilled off under reduced pressure. The residue was subjected to silica gel column chromatography and elution with an n-hexane/ethyl acetate (7:1) solution followed by conventional hydrolysis to give 0.28 g (32%) of compound (12) of interest as yellow oil.

Example 6

Production of 2-[2-fluoro-4-((1S,2S)-2-hydroxycyclo-pentyloxy)phenyl]propionic acid (13)

To a solution of compound (8) (3.50 g, 17.7 mmol) in dry DMF (35 mL), cyclopentene oxide (2.3 mL, 26.6 mmol) and sodium hydride (0.64 g, 26.6 mmol) were added and stirred at 70° C. for 14 hours. After completion of the reaction, the obtained mixture was cooled to room temperature and concentrated under reduced pressure. The residue was extracted with ethyl acetate (300 mL) followed by washing with water and drying (over sodium sulfate). The solvent was distilled off, and the residue was subjected to silica gel column chromatography and elution with an n-hexane/ethyl acetate (8:1) solution followed by conventional hydrolysis to give 2.60 g (52%) of compound (13) of interest as yellow oil.

Example 7

Production of 2-[4-(cyclopentyloxy)-2-fluorophenyl]-propionic acid (14)

To a solution of compound (8) (0.50 g, 2.5 mmol) in dry DMF (5 mL), potassium carbonate (1.2 g, 8.8 mmol), and bromocyclopentane (0.32 g, 3.0 mmol) were added and stirred at 60° C. for 5 hours. The reaction mixture was filtered and the filtrate was concentrated under reduced pressure. The residue was extracted with ethyl acetate (300 mL) followed by washing with water and drying (over sodium sulfate). The solvent was distilled off, and the residue was dissolved in dichloromethane and washed with a 1 M-aqueous solution (30 mL) of sodium hydroxide. The organic layer was dried (over sodium sulfate) and distilled off under reduced pressure. The obtained residue was subjected to silica gel column chromatography and elution with an n-hexane/ethyl acetate (4:1) solution followed by conventional hydrolysis to give 0.56 g (84%) of compound (14) of interest as white solid.

Example 8

Production of 2-[2-fluoro-4-(2-oxocyclopentylthio)-phenyl]propionic acid (15)

To a solution of compound (9) (0.54 g, 2.5 mmol) obtained above in dichloromethane (25 mL), cyclopentanone (0.19 mL, 2.1 mmol) and N-bromosuccinimide (0.31 g, 2.3 mmol) were added at 0° C. and stirred at room temperature for 4 hours. To the mixture, dichloromethane was added, and the organic layer was washed with saline, dried (over sodium sulfate), and then distilled off under reduced pressure. The residue was subjected to silica gel column chromatography and elution with an n-hexane/ethyl acetate (8:1) solution followed by conventional hydrolysis to give 0.27 g (36%) of compound (15) of interest as yellow oil.

Example 9

Production of 2-[2-fluoro-4-((1S,2S)-2-hydroxycyclo-pentylthio)phenyl]propionic acid (16)

To an aqueous solution (19 mL) of borax (0.1 g, 0.26 mmol), 1,2-epoxycyclopentene (0.8 mL, 9.3 mmol) and compound (9) (1.60 g, 7.5 mmol) were sequentially added. The mixture was stirred at room temperature for 39 hours and dichloromethane (50 mL) was added thereto. The organic layer was washed with water and dried (over sodium sulfate). The solvent was distilled off, and the residue was subjected to silica gel column chromatography and elution with an n-hexane/ethyl acetate (8:1) solution followed by conventional hydrolysis to give 1.79 g (84%) of compound (16) of interest as yellow oil.

Example 10

Production of 2-[4-(cyclopentylthio)-2-fluoro-phenyl]propionic acid (17)

A solution of compound (9) (0.53 g, 2.5 mmol), bromocyclopentane (0.32 mL, 3.0 mmol), and potassium carbonate (1.2 g, 8.8 mmol) in dry DMF (5 mL) was treated in the same manner as in Example 7. The obtained residue was subjected to silica gel column chromatography and elution with an n-hexane/ethyl acetate (4:1) solution followed by conventional hydrolysis to give 0.64 g (90%) of compound (17) of interest as white solid.

Production Example 2

Production of Intermediates (18) to (20)

(a) Production of methyl 2-[fluoro-4-(trifluoromethyl-sulfonyloxy)phenyl]propionate (18)

To a solution of compound (8) (3.69 g, 14.9 mmol) and triethylamine (4.13 mL, 29.7 mmol) in dry dichloromethane, $(CF_3SO_2)_2O$ (2.93 mL, 17.8 mmol) was added dropwise at 0° C. After completion of the dropwise addition, the mixture was stirred at room temperature for 12 hours. The organic layer was washed sequentially with a 1M aqueous solution (90 mL) of hydrochloric acid, a 1M aqueous solution of sodium hydroxide (90 mL), and saline (90 mL), and dried (over sodium sulfate). The solvent was then distilled off. The obtained residue was subjected to silica gel column chromatography and elution with an n-hexane/ethyl acetate (10:1) solution to give 5.44 g (96%) of compound (18) of interest as clear yellow liquid matter.

(b) Production of methyl (2-fluoro-4-methylphenyl)propionate (19)

To a suspension of [1,2-bis(diphenylphospino)ethane]-dichloropalladium(II) [Pd(dppe)Cl$_2$] (14.1 mg and 1.3 mol %) in dry 1,4-dioxane (3 mL), a solution of compound (18) (0.62 g, 1.9 mmol) in dry 1,4-dioxane (3 mL) was added dropwise under argon gas flow. To this suspension, dimethyl zinc (2M-solution in toluene, 9.0 mL, 2.0 mmol) was slowly added dropwise. After completion of the dropwise addition, the suspension was heated to reflux for 4 hours. After cooling, methanol (0.4 mL) was added thereto and the mixture was treated with ether. The organic layer was washed with a 1M aqueous solution (18 mL) of hydrochloric acid and dried (over sodium sulfate), and the solvent was distilled off. The obtained residue was subjected to silica gel column chromatography and elution with an n-hexane/ethyl acetate (10:1) solution to give 0.26 g (70%) of compound (19) of interest as colorless liquid matter.

This compound was identified as an authentic sample on the basis of the data of instrumental analysis.

(c) Production of methyl 2-[4-(bromomethyl)-2-fluorophenyl]-propionate (20)

Compound (20) was produced according to the method described in J. Med. Chem., 53, 7879 (2010). The obtained compound (20) of interest was identified on the basis of the data of instrumental analysis of the authentic sample.

Example 11

Production of 2-[2-fluoro-4-(furan-2-ylmethyl)-phenyl]propionic acid (21a)

Compound 20 (0.88 g, 3.2 mmol) and 2-furan boronic acid (0.54 g, 4.8 mmol) were dissolved in tetrahydrofuran (12 mL) and a 2 M-aqueous solution (4.0 mL) of sodium carbonate. To this solution, trans-bromo(N-succinimidyl)bis(triphenylphosphine)palladium(II) [trans-PdBr(N-Succ)(PPh$_3$)$_2$] (25.9 mg, 1.0 mol %) was added and heated to reflux for 3 hours. After cooling to room temperature and adding ether (50 mL) to the solution, the organic layer was washed with water (30 mL) and dried (over magnesium sulfate), and the solvent was distilled off. The obtained residue was subjected to silica gel column chromatography and elution with an n-hexane/ethyl acetate (20:1) solution followed by conventional hydrolysis with potassium hydroxide to give 0.36 g (43%) of compound (21a) of interest as white solid.

Example 12

Production of 2-[2-fluoro-4-(thiophene-2-ylmethyl)-phenyl]propionic acid (21b)

Compound 20 (0.98 g, 3.8 mmol) and 2-thiopheneboronic acid (0.73 g, 5.7 mmol) were dissolved in tetrahydrofuran (12 mL) and a 2 M-aqueous solution (4.8 mL) of sodium carbonate. To this solution, trans-bromo(N-succinimidyl)bis(triphenylphosphine)palladium(II) [trans-PdBr(N-Succ) (PPh$_3$)$_2$] (30.8 mg, 1.0 mol %) was added and treated in the same manner as in Example 11. The obtained residue was subjected to silica gel column chromatography and elution with an n-hexane/ethyl acetate (20:1) solution followed by conventional hydrolysis with potassium hydroxide to give 0.75 g (76%) of compound (21b) of interest as white solid.

Example 13

Production of 2-[2-fluoro-4-(furan-3-ylmethyl)-phenyl]propionic acid (22a)

Compound 20 (0.88 g, 3.2 mmol) and 3-furanboronic acid (0.54 g, 4.8 mmol) were dissolved in tetrahydrofuran (12 mL) and a 2 M-aqueous solution (4.0 mL) of sodium carbonate. To this solution, trans-bromo(N-succinimidyl)bis(triphenylphosphine)palladium(II) [trans-PdBr(N-Succ)(PPh$_3$)$_2$] (25.9 mg, 1.0 mol %) was added and treated in the same manner as in Example 11. The obtained residue was subjected to silica gel column chromatography and elution with an n-hexane/ethyl acetate (20:1) solution followed by conventional hydrolysis with potassium hydroxide to give 0.46 g (55%) of compound (22a) of interest as white solid.

Example 14

Production of 2-[2-fluoro-4-(thiophene-3-ylmethyl)-phenyl]propionic acid (22b)

Compound 20 (0.88 g, 3.2 mmol) and 2-thiopheneboronic acid (0.87 g, 3.4 mmol) were dissolved in tetrahydrofuran (12 mL) and a 2 M-aqueous solution (4.2 mL) of sodium carbonate. To this solution, trans-bromo(N-succinimidyl)bis(triphenylphosphine)palladium(II) [trans-PdBr(N-Succ)(PPh$_3$)$_2$] (27.5 mg, 1.0 mol %) was added and treated in the same manner as in Example 11. The obtained residue was subjected to silica gel column chromatography and elution with an n-hexane/ethyl acetate (20:1) solution followed by conventional hydrolysis with potassium hydroxide to give 0.75 g (85%) of compound (22b) of interest as white solid.

Example 15

Production of 2-[4-(ethyl-3-oxobutyl)-2-fluoro-phenyl]propionic acid (23)

To a suspension of anhydrous potassium carbonate (0.86 g, 6.2 mmol) in acetone (40 mL), ethyl 2-ethylacetoacetate (0.56 mL, 3.45 mmol) was added under stirring. After stirring for 15 minutes at room temperature, compound (20) (0.95 g, 3.45 mmol) was added, and the reaction mixture was refluxed for 12 hours. After cooling, the reaction mixture was concentrated under reduced pressure, and the residue was treated with dichloromethane (50 mL). The organic layer was washed with a sodium bicarbonate solution and saline, and the solvent was distilled off. The obtained residue was subjected to silica gel column chromatography and elution with an n-hexane/ethyl acetate (7:2) solution followed by conventional decarboxylation and hydrolysis to give 0.55 g (45%) of compound (23) of interest as clear colorless oil.

Example 16

Production of 2-[2-fluoro-4-(2-methyl-3-oxopentyl)-phenyl]propionic acid (24)

A suspension of compound (20) (0.78 g, 2.82 mmol), ethyl 2-methyl-3-oxopentanoate (0.46 mL, 2.82 mmol) and anhydrous potassium carbonate (0.70 g, 5.1 mmol) in acetone (40 mL) was allowed to react in the same manner as in Example 15. The obtained residue was subjected to silica gel column chromatography and elution with an n-hexane/ethyl acetate (7:2) solution followed by conventional decarboxylation and hydrolysis to give 0.53 g (53%) of compound (24) of interest as clear colorless oil.

Production Example 3

Production of Intermediate Compounds

Intermediates in Reaction Scheme 4

(a) Production of diethyl 2-(2,5-difluoro-4-nitrophenyl)-2-methylmalonate (26a)

A solution of commercially available 2,4,5-trifluoro-nitrobenzene (25a) (5.0 mL, 43.5 mmol), diethyl methylmalonate (6.2 mL, 36.1 mmol), and sodium hydroxide (1.57 g, 39.1 mmol) in DMF (55 mL) was allowed to react in the same manner as in (a) in Production Example 1. The crude product was subjected to silica gel column chromatography and elution with an n-hexane/ethyl acetate (10:1) solution to give 11.0 g (76%) of compound (26a) of interest as clear brown oil.

(b) Production of diethyl 2-(2,6-difluoro-4-nitrophenyl)-2-methylmalonoate (26b)

A solution of commercially available 3,4,5-trifluoro-nitrobenzene (25b) (5.0 mL, 42.8 mmol), diethyl methylmalonate (6.1 mL, 35.7 mmol), and sodium hydroxide (1.54 g, 38.5 mmol) in DMF (55 mL) was allowed to react in the same manner as in (a) in Production Example 1. The crude product was subjected to silica gel column chromatography and elution with an n-hexane/ethyl acetate (10:1) solution to give 9.1 g (63%) of compound (26b) of interest as clear brown oil.

(c) Production of 2-(2,5-difluoro-4-nitrophenyl)propionic acid (27a)

A solution of compound (26a) (10.8 g, 32.6 mmol) in acetic acid (36 mL), and concentrated sulfuric acid (10 mL), and water (26 mL) were treated in the same manner as in (b) in Production Example 1 to give 6.2 g (82%) of compound (27a) as yellow solid.

This product was allowed to undergo the following reaction, without purification.

(d) Production of 2-(2,6-difluoro-4-nitrophenyl)propionic acid (27b)

A solution of compound (26b) (7.8 g, 24.9 mmol) in acetic acid (28 mL), and concentrated sulfuric acid (8.0 mL), and water (20 mL) were treated in the same manner as in (b) in Production Example 1 to give 4.9 g (85%) of compound (27b) as yellow solid.

This product was allowed to undergo the following reaction, without purification.

(e) Production of methyl 2-(2,5-difluoro-4-nitrophenyl)propionate (28a)

Compound (27a) (6.2 g, 26.8 mmol) was dissolved in a solution of a catalytic amount of concentrated hydrochloric acid (0.24 mL) in methanol (123 mL) and treated in the same manner as in (c) in Production Example 1 to give 5.9 g (90%) of compound (28a) as pale yellow oil.

This product was allowed to undergo the following reaction, without purification.

(f) Production of methyl 2-(2,6-difluoro-4-nitrophenyl)propionate (28b)

Compound (27b) (3.6 g, 15.6 mmol) was dissolved in a solution of a catalytic amount of concentrated hydrochloric acid (0.14 mL) in methanol (72 mL) and treated in the same manner as in (c) in Production Example 1 to give 3.4 g (89%) of compound (28b) as pale yellow oil.

This product was allowed to undergo the following reaction, without purification.

(g) Production of methyl 2-(4-amino-2,5-difluorophenyl)propionate (29a)

To a solution of compound (28a) (5.2 g, 21.2 mmol) in ethanol (96 mL), 10% palladium-carbon (0.52 g, 10% w/w) was added and treated under hydrogen gas flow in the same manner as in (d) in Production Example 1 to give 3.5 g (83%) of compound (29a) as red oil.

This product was allowed to undergo the following reaction, without purification.

(h) Production of methyl 2-(4-amino-2,6-difluorophenyl)propionate (29b)

To a solution of compound (28a) (3.4 g, 13.9 mmol) in ethanol (80 mL), 10% palladium-carbon (0.34 g, 10% w/w) was added and treated under hydrogen gas flow in the same manner as in (d) in Production Example 1 to give 2.3 g (84%) of compound (29b) as red oil.

This product was allowed to undergo the following reaction, without purification.

(i) Production of methyl 2-(4-bromo-2,5-difluorophenyl)propionate (30a)

To a solution of compound (29a) (3.0 g, 13.9 mmol) in 40% hydrobromic acid (8.0 mL, 54.4 mmol), an aqueous solution (17 mL) of sodium nitrite (1.1 g, 15.7 mmol) was added dropwise under stirring at 0 to 5° C. The solution was allowed to reach room temperature. To the solution, CuBr (1.1 g, 11.2 mmol) and 96% sulfuric acid (0.1 mL) were added, and the mixture was refluxed under stirring for 1 hour. After cooling and subsequent extraction with ethyl acetate, the obtained residue was dissolved in methanol (50 mL). To the obtained mixture, a catalytic amount of concentrated hydrochloric acid (0.1 mL) was added and refluxed for 3 hours. After cooling, the solvent was distilled off and the obtained product was treated with ether (50 mL). The organic layer was dried (over sodium sulfate) and the solvent was distilled off. The obtained residue was subjected to silica gel column chromatography and elution with an n-hexane/ethyl acetate (4:1) solution to give 3.01 g (73%) of compound (30a) as pale yellow liquid matter.

(j) Production of methyl 2-(4-bromo-2,6-difluorophenyl)propionate (30b)

A solution of compound (29b) (6.7 g, 31.3 mmol) in 40% hydrobromic acid (18.4 mL, 125 mmol) was treated with an aqueous solution (38 mL) of sodium nitrite (2.4 g, 33.8 mmol), CuBr (2.5 g, 17.5 mmol), and 96% sulfuric acid (0.1 mL) in the same manner as in (i) above. The obtained product was further dissolved in methanol (100 mL), and a catalytic amount of concentrated hydrochloric acid (0.2 mL) was added thereto and treated in the same manner. The obtained residue was subjected to silica gel column chromatography and elution with an n-hexane/ethyl acetate (4:1) solution to give 6.1 g (70%) of compound (30b) as pale yellow liquid matter.

(k) Production of methyl 2-(2,5-difluoro-4-methylphenyl)propionate (31a)

To a solution of trans-dibromobis(triphenylphosphine)-palladium(II) [trans-Pd(PPh$_3$)$_2$Br$_2$] (0.048 g, 5.6 mol %) in 1,4-dioxane (30 mL), a solution of compound (30a) (3.0 g, 10.7 mmol) in dry 1,4-dioxane (4 mL) was added under argon gas flow. To this mixture, dimethyl zinc (2M-solution in toluene, 11.0 mL, 22.0 mmol) was slowly added dropwise and the reaction mixture was heated to reflux for 4 hours. After cooling the reaction mixture to room temperature, methanol (4.0 mL) was added to the reaction mixture and the obtained mixture was diluted with diethyl ether. The organic layer was washed with a 1M aqueous solution (34 mL) of hydrochloric acid and dried (over magnesium sulfate). The solvent was distilled off, and the obtained residue was subjected to silica gel column chromatography and elution with an n-hexane/ethyl acetate (4:1) solution to give 3.3 g (83%) of compound (31a) as colorless liquid matter.

(l) Production of methyl 2-(2,6-difluoro-4-methylphenyl)propionate (31b)

Compound (30b) (5.4 g, 19.3 mmol) and dimethyl zinc (2M-solution in toluene, 38.7 mL, 77.4 mmol), and a solution (40 mL) of trans-dibromobis(triphenylphosphine)palladium (II) [trans-Pd(PPh$_3$)$_2$Br$_2$] (0.085 g, 5.6 mol %) in 1,4-dioxane (40 mL) were treated in the same manner as in (k) above. The obtained crude product was subjected to silica gel column chromatography and elution with an n-hexane/ethyl acetate (4:1) solution to give 3.2 g (77%) of compound (31b) as colorless oil.

(m) Production of methyl 2-[4-(bromomethyl)-2,5-difluoro-phenyl]propionate (32a)

A solution of compound (31a) (3.3 g, 15.4 mmol) in carbon tetrachloride (100 mL) was treated with N-bromosuccinimide (NBS) (3.3 g, 18.5 mmol) in the presence of a catalytic amount of azo(bis)isobutyronitrile (AIBN) (0.05 g, 0.02 mmol). The obtained crude product was subjected to silica gel column chromatography and elution with an n-hexane/ethyl acetate (4:1) solution to give 4.8 g (90%) of compound (32a) as clear red oil.

(n) Production of methyl 2-[4-(bromomethyl)-2,6-difluoro-phenyl]propionate (32b)

A solution of compound (31b) (2.3 g, 10.7 mmol) in carbon tetrachloride (70 mL) was treated with NBS (2.3 g, 12.9 mmol) in the presence of a catalytic amount of AIBN (0.04 g, 0.02 mmol). The obtained crude product was subjected to silica gel column chromatography and elution with an n-hexane/ethyl acetate (4:1) solution to give 2.7 g (86%) of compound (32b) as clear red oil.

Example 17

Production of 2-[2,5-difluoro-4-(2-oxocyclo-pentylmethyl)phenyl]propionic acid (33a)

Compound (32a) (4.8 g, 16.4 mmol), methyl 2-oxocyclopentanecarboxylate (2.5 mL, 21.9 mmol), and anhydrous potassium carbonate (4.0 g, 28.9 mmol) in acetone (200 mL) were allowed to react in the same manner as in Example 15. The obtained crude product was subjected to silica gel column chromatography and elution with an n-hexane/ethyl acetate (4:1) solution followed by conventional decarboxylation and hydrolysis to give 3.5 g (60%) of compound (33a) of interest as clear yellow oil.

Example 18

Production of 2-[2,6-difluoro-4-(2-oxocyclo-pentylmethyl)phenyl]propionic acid (33b)

Compound (32b) (2.2 g, 7.5 mmol), methyl 2-oxocyclopentane-carboxylate (1.3 mL, 11.3 mmol), and anhydrous potassium carbonate (1.9 g, 13.6 mmol) in acetone (100 mL) were allowed to react in the same manner as in Example 15. The obtained crude product was subjected to silica gel column chromatography and elution with an n-hexane/ethyl acetate (4:1) solution followed by conventional decarboxylation and hydrolysis to give 1.7 g (64%) of compound (33b) of interest as clear yellow oil.

Production Example 4

Production of Intermediate Compounds

Intermediates in Reaction Scheme 5

(a) Production of 2-bromo-6-fluoro-4-methylbenzaldehyde (35)

Compound (34) was formylated according to the method described in J. Med. Chem., 53, 7879 (2010) to give compound (35) as brown oil (38%).

(b) Production of 2-bromo-6-fluoro-4-methylphenyl acetic acid (36)

Compound (35) obtained above was subjected to Wittig reaction and oxidation with pyridinium fluorochromate (PFC) according to the method described in J. Med. Chem., 53, 7879 (2010) to give compound (36) as a white solid (60% in two stages).

(c) Production of methyl 2-(2-bromo-6-fluoro-4-methylphenyl)-propionate (37)

Compound (36) obtained above was subjected to esterification and α-methylation according to the method described in J. Med. Chem., 53, 7879 (2010) to give compound (37) as a clear yellow liquid matter (66% in 2 stages).

(d) Production of methyl 1-[3-bromo-5-fluoro-4-(1-methoxy-1-oxopropane-2-yl)benzyl]-2-oxocyclopentanecarboxylate (38)

Compound (37) obtained above was subjected to α-bromination and acetoacetic ester synthesis in the same manner as in (c) in Production Example 2 to give compound (38) as clear colorless liquid matter (54% in 2 stages).

Example 19

Production of 2-[2-bromo-6-fluoro-4-{(2-oxocyclopentyl)methyl}phenyl]propanoic acid (39)

Compound (38) obtained above was subjected decarboxylation and hydrolysis according to the method described in J. Med. Chem., 53, 7879 (2010) to give compound (39) as clear yellow liquid matter (86%).

Example 20

Production of 2-{3-fluoro-4'-hydroxy-5-[(2-oxocyclopentyl)methyl]biphenyl-2-yl}bromo-6-fluoro-4-{(2-oxocyclopentyl)methyl}phenyl]propionic acid (40)

Compound (39) obtained above was subjected to Suzuki-miyaura cross-coupling reaction with 4-hydroxyphenylboronic acid according to the method described in Bioorg. Med. Chem., 19, 3299 (2011) to give compound (40) as white solid (47% in 3 stages).

The chemical structural formulas and physical data of respective intermediate compounds obtained above in Production Examples 1 to 4 were summarized in Tables 1 to 5 below.

The chemical structural formulas, properties, and physical data of the 2-fluorophenyl propionic acid derivatives of the present invention, which were of interest and obtained in respective Examples described above, were summarized, in Tables 6 to 11 below.

TABLE 1

| Compd. No. | Chemical Structure | Physical Data |
|---|---|---|
| 4 | $O_2N$-phenyl(F)-C(CH_3)(COOC_2H_5)_2 | $^1$H-NMR (CDCl$_3$) δ: 1.28 (6H, t, J = 6.9 Hz), 1.89 (3H, s), 4.19-4.36 (4H, m). 7.45 (1H, t, J = 7.3 Hz). 7.95 (1H, dd, J = 2.6, 13.2 Hz), 8.01-8.05 (1H, m), $^{13}$C-NMR (CDCl$_3$) δ: 13.8, 14.0, 21.7, 56.8, 61.2, 62.4, 111.5, 119.9, 119.1, 128.7, 134.6, 148.0 (d, J$_{C-F}$ = 254 Hz), 160.2, 169.4. FAB-MS (m/z): 313.10 (M$^+$, Calcd for C$_{14}$H$_{16}$FNO$_6$: 313.10). |
| 5 | $O_2N$-phenyl(F)-CH(CH_3)-COOH | $^1$H-NMR (CDCl$_3$) δ: 1.60 (3H, d, J = 7.3 Hz), 4.14 (1H, q, J = 7.3 Hz), 7.45 (1H, t, J = 7.3 Hz), 7.54 (1H, t, J = 8.4 Hz), 7.94 (1H, dd, J = 2.2, 11.7 Hz), 8.03-8.05 (1H, m). 11.15 (1H, brs). (CDCl$_3$) δ: 16.8, 38.7, 111.6, 119.5, 129.7, 134.5, 147.8, 159.8 (d, J$_{C-F}$ = 251 Hz), 178.9. FAB-MS (m/z): 213.10 (M$^+$, Calcd for C$_9$H$_8$FNO$_4$: 213.04). |
| 6 | $O_2N$-phenyl(F)-CH(CH_3)-COOCH_3 | $^1$H-NMR (CDCl$_3$) δ: 1.56 (3H, d, J = 7.3 Hz), 3.71(3H, s), 4.10 (1H, q, J = 7.3 Hz), 7.52 (1H, t, J = 7.3 Hz), 7.94 (1H, dd, J = 2.2, 12.1 Hz), 8.02-8.06 (1H, m). $^{13}$C-NMR (CDCl$_3$) δ: 17.2, 38.5, 52.4, 111.5, 119.4, 129.6, 135.4, 147.6, 159.7 (d, J$_{C-F}$ = 250 Hz), 172.9. FAB-MS (m/z): 227.10 (M$^+$, Calcd for C$_{10}$H$_{10}$FNO$_4$: 227.06). |

TABLE 1-continued

| Compd. No. | Chemical Structure | Physical Data |
|---|---|---|
| 7 | $H_2N$-phenyl(F)-CH(CH_3)-COOCH_3 | $^1$H-NMR (CDCl$_3$) δ: 1.44 (3H, d, J = 6.9 Hz), 3.66 (3H, s), 3.81 (2H, s), 3.90 (1H, q, J = 7.3 Hz), 6.34-6.44 (2H, m), 7.03 (1H, t, J = 8.4 Hz). $^{13}$C-NMR. (CDCl$_3$) δ: 17.6, 37.5, 52.0, 101.9, 111.0, 117.1, 129.0, 147.0, 159.4 (d, J$_{C-F}$ = 244 Hz), 174.9. FAB-MS (m/z): 197.08 (M$^+$, Calcd for C$_{10}$H$_{12}$FNO$_2$: 197.08). |
| 8 | HO-phenyl(F)-CH(CH_3)-COOCH_3 | $^1$H-NMR (CDCl$_3$) δ 1.48 (3H, d, J = 7.0 Hz), 3.70 (3H, s), 3.81 (2H, S), 3.96 (1H, q, J = 7.3 Hz), 6.50-6.57 (2H, m), 7.05 (1H, t, J = 8.4 Hz). $^{13}$C-NMR. (CDCl$_3$) δ 17.6, 37.9, 52.4, 103.1, 111.5, 118.9, 128.9, 156.3, 160.7 (d, J$_{C-F}$ = 245 Hz), 175.9. FAB-MS (m/z): 198.10 (M$^+$, Calcd for C$_{10}$H$_{11}$FO$_3$: 198.07). |

TABLE 2

| Compd. No. | Chemical Structure | Physical Data |
|---|---|---|
| 9 | HS-phenyl(F)-CH(CH_3)-COOCH_3 | $^1$H-NMR (CDCl$_3$) δ: 1.47 (d, 3H, J = 7.3 Hz), 3.49 (s, 1H), 3.97 (q, 1H, J = 7.3 Hz), 6.96-7.03 (m, 2H), 7.18 (t, 1H, J = 7.8 Hz). $^{13}$C-NMR (CDCl$_3$) δ: 17.5, 37.9, 52.2, 116.3, 125.3, 129.3, 143.90, 152.5, 160.9 (d, J$_{C-F}$ = 245 Hz), 165.9. FAB-MS (m/z): 215.20 (M$^+$ +H, Calcd for C$_{10}$H$_{12}$FO$_2$S: 215.05). |
| 18 | $F_3C$-$SO_2$-O-phenyl(F)-CH(CH_3)-COOCH_3 | 1H-NMR (CDCl$_3$) δ: 1.52 (3H, d, J = 7.3 Hz), 3.70 (3H, s), 4.03 (1H, q, J = 7.3 Hz), 7.02-7.11 (2H, m), 7.41 (1H, t, J = 8.2 Hz). $^{13}$C-NMR (CDCl$_3$) δ: 17.5, 38.0 (d, J$_{C-F}$ = 1.9 Hz), 52.4, 109.7 (d, J$_{C-F}$ = 27.3 Hz), 116.5, 117.4 (d, J$_{C-F}$ = 3.7 Hz), 128.6 (d, J$_{C-F}$ = 14.9 Hz), 130.0 (d, J$_{C-F}$ = 5.6 Hz), 148.3 (d, J$_{C-F}$ = 11.2 Hz), 160.6 (d, J$_{C-F}$ = 252 Hz), 173.5. FAB-MS (m/z): 330.88 (M$^+$, Calcd for C$_{11}$H$_{10}$F$_4$O$_5$S: 330.02). |

TABLE 2-continued

| Compd. No. | Chemical Structure | Physical Data |
|---|---|---|
| 26a | [Structure: benzene ring with $O_2N$, two F, $COOC_2H_5$ (×2), $CH_3$ substituents] | $^1$H-NMR (CDCl$_3$) δ: 1.29 (6H, t, J = 7.1 Hz), 1.87 (3H, s), 4.24-4.34 (4H, m), 7.29 (1H, dd, J = 11.0, 6.2 Hz), 7.82 (1H, dd, J = 9.9, 6.2 Hz). $^{13}$C-NMR (CDCl$_3$) δ: 13.8 (d, $J_{C-F}$ = 1.2 Hz), 21.7, 56.6, 62.6, 113.4 (dd, $J_{C-F}$ = 31.1, 2.5 Hz), 118.3 (dd, $J_{C-F}$ = 24.9, 3.7 Hz), 136.0 (dd, $J_{C-F}$ = 7.5, 3.7 Hz), 149.6 (d, $J_{C-F}$ = 2.5 Hz), 153.0, 155.5 (d, $J_{C-F}$ = 250 Hz), 168.9. FAB-MS (m/z): 332.27 (M$^+$+H, Calcd for C$_{14}$H$_{16}$F$_2$NO$_6$: 332.09). |
| 26b | [Structure: benzene ring with $O_2N$, two F, $COOC_2H_5$ (×2), $CH_3$ substituents] | $^1$H-NMR. (CDCl$_3$) δ: 1.27 (6H, t, J = 7.1 Hz), 1.86 (3H, s), 4.19-4.36 (4H, m), 7.77-7.83 (2H, m). $^{13}$C-NMR (CDCl$_3$) δ: 13.8, 21.4 (d, $J_{C-F}$ = 2.5 Hz), 108.1 (dd, $J_{C-F}$ = 30.5, 3.1 Hz), 160.1 (d, $J_{C-F}$ = 254 Hz), 160.2 (dd, $J_{C-F}$ = 253 Hz), 168.5. FAB-MS (m/z): 332.26 (M$^+$+H, Calcd for C$_{14}$H$_{16}$F$_2$NO$_6$: 332.09). |
| 27a | [Structure: benzene ring with $O_2N$, two F, COOH, $CH_3$ substituents] | $^1$H-NMR (CDCl$_3$) δ: 1.60 (3H, d, J = 7.3 Hz), 4.11 (1H, q, J = 7.2 Hz), 7.32 (1H, dd, J = 11.0, 5.9 Hz), 7.82 (1H, dd, J = 8.8, 5.9 Hz), 10.72 (1H, brs). $^{13}$C NMR (CDCl$_3$) δ: 16.8, 38.6, 113.2 (dd, $J_{C-F}$ = 29.9, 2.5 Hz), 118.7 (dd, $J_{C-F}$ = 23.7, 5.0 Hz), 135.7 (dd, $J_{C-F}$ = 8.3, 4.2 Hz), 150.1 (d, $J_{C-F}$ = 3.7 Hz), 155.1 (dd, $J_{C-F}$ = 248, 3.7 Hz), 178.2. FAB-MS (m/z): 232.18 (M$^+$+H, Calcd for C$_9$H$_8$F$_2$NO$_4$: 232.04). |

TABLE 3

| Compd. No. | Chemical Structure | Physical Data |
|---|---|---|
| 27b | [Structure: benzene ring with $O_2N$, two F, COOH, $CH_3$ substituents] | $^1$H-NMR. (CDCl$_3$) δ: 1.58 (3H, d, J = 7.3 Hz), 4.23 (1H, q, J = 7.3 Hz), 7.78-7.86 (2H, m), 10.53 (1H, brs). $^{13}$C-NMR (CDCl$_3$) δ: 15.5, 34.8, 107.8 (dd, $J_{C-F}$ = 10.4, 5.2 Hz), 123.9 (t, $J_{C-F}$ = 18.7 Hz), 147.6 (t, $J_{C-F}$ = 7.5 Hz), 160.4 (dd, $J_{C-F}$ = 253, 8.7 Hz), 177.8. FAB-MS (m/z): 232.20 (M$^+$+H, Calcd for C$_9$H$_8$F$_2$NO$_4$: 232.04). |
| 28a | [Structure: benzene ring with $O_2N$, two F, $COOCH_3$, $CH_3$ substituents] | $^1$H-NMR (CDCl$_3$) δ: 1.56 (3H, d, J = 7.1 Hz), 3.74 (3H, s), 4.06 (1H, d, J = 7.3 Hz), 4.11 (1H, d, J = 7.3 Hz), 7.33 (1H, dd, J = 11.1, 6.0 Hz), 7.81 (1H, dd, J = 8.8, 6.0 Hz). $^{13}$C-NMR (CDCl$_3$) δ: 17.2, 38.5, 52.6 (d, $J_{C-F}$ = 1.2 Hz), 113.0 (dd, $J_{C-F}$ = 28.6, 2.5 Hz), 118.6 (dd, $J_{C-F}$ = 24.3, 4.4 Hz), 136.7 (dd, $J_{C-F}$ = 8.3, 4.2 Hz), 151.7 (dd, $J_{C-F}$ = 252, 2.5 Hz), 155.1 (dd, $J_{C-F}$ = 237, 2.5 Hz), 172.3. FAB-MS (m/z): 246.23 (M$^+$+H, Calcd for C$_{10}$H$_{10}$F$_2$NO$_4$: 246.06). |
| 28b | [Structure: benzene ring with $O_2N$, two F, $COOCH_3$, $CH_3$ substituents] | $^1$H-NMR (CDCl$_3$) δ: 1.56 (3H, d, J = 7.3 Hz), 3.73 (3H, s), 4.15 (1H, d, J = 7.3 Hz), 7.81 (1H, dt, J = 14.9, 3.7 Hz), 7.81 (1H, dd, J = 8.8, 6.0 Hz). $^{13}$C-NMR (CDCl$_3$) δ: 15.8 (d, $J_{C-F}$ = 3.7 Hz), 34.7 (d, $J_{C-F}$ = 2.5 Hz), 52.6, 107.7 (dd, $J_{C-F}$ = 10.0, 5.0 Hz), 124.8 (t, $J_{C-F}$ = 18.7 Hz), 147.4, 160.4 (dd, $J_{C-F}$ = 252, 8.7 Hz), 171.7. FAB-MS (m/z): 246.22 (M$^+$+H, Calcd for C$_{10}$H$_{10}$F$_2$NO$_4$: 246.06). |
| 29a | [Structure: benzene ring with $H_2N$, two F, $COOCH_3$, $CH_3$ substituents] | $^1$H-NMR (CDCl$_3$) δ: 1.44 (3H, d, J = 7.1 Hz), 3.67 (3H, s), 3.85 (2H, brs), 3.89 (1H, q, J = 8.4 Hz), 6.45 (1H, dd, J = 10.8, 7.5 Hz), 6.91 (1H, dd, J = 11.4, 6.6 Hz). $^{13}$C-NMR (CDCl$_3$) δ: 17.5, 37.3 (d, $J_{C-F}$ = 2.5 Hz), 52.0, 103.3 (dd, $J_{C-F}$ = 28.0, 4.4 Hz), 114.4 (dd, $J_{C-F}$ = 21.8, 5.6 Hz), 116.4 (dd, $J_{C-F}$ = 17.4, 6.2 Hz), 134.6 (dd, $J_{C-F}$ = 14.9, 12.5 Hz), 147.5 (dd, $J_{C-F}$ = 234, 2.5 Hz), 156.3 (dd, $J_{C-F}$ = 240, 2.5 Hz), 174.5. FAB-MS (m/z): 215.20 (M$^+$, Calcd for C$_{10}$H$_{11}$F$_2$NO$_2$: 215.08). |
| 29b | [Structure: benzene ring with $H_2N$, two F, $COOCH_3$, $CH_3$ substituents] | $^1$H-NMR (CDCl$_3$) δ: 1.46 (3H, d, J = 7.3 Hz), 3.68 (3H, s), 3.89 (2H, brs), 3.93 (1H, q, J = 7.1 Hz), 6.17 (1H, dt, J = 17.2, 3.6 Hz). $^{13}$C-NMR (CDCl$_3$) δ: 16.5, 33.9, 52.1, 97.9 (dd, $J_{C-F}$ = 9.5, 4.8 Hz), 106.3 (t, $J_{C-F}$ = 19.3 Hz), 147.3 (t, $J_{C-F}$ = 13.7 Hz), 161.5 (dd, $J_{C-F}$ = 244, 11.2 Hz), 174.0. FAB-MS (m/z): 215.23 (M+, Calcd for C$_{10}$H$_{11}$F$_2$NO$_2$: 215.08). |

TABLE 4

| Compd. No. | Chemical Structure | Physical Data |
|---|---|---|
| 30a | (4-bromo-2,5-difluorophenyl, methyl 2-arylpropanoate) | 1H-NMR. (CDCl₃) δ: 1.49 (3H, d, J = 7.1 Hz), 3.70 (3H, s), 3.97 (1H, q, J = 7.3 Hz), 7.10 (1H, dd, J = 8.8, 6.2 Hz), 7.27 (1H, dd, J = 8.7, 5.8 Hz). $^{13}$C-NMR (CDCl₃) δ: 17.4, 38.1, 52.5 (d, $J_{C-F}$ = 10.0 Hz), 107.6 (dd, $J_{C-F}$ = 24.3, 9.3 Hz), 114.6 (dd, $J_{C-F}$ = 26.2, 3.7 Hz), 116.0 (dd, $J_{C-F}$ = 25.5, 4.4 Hz), 120.3 (d, $J_{C-F}$ = 27.4 Hz), 128.8 (dd, $J_{C-F}$ = 17.4, 6.2 Hz), 155.6 (dd, $J_{C-F}$ =244, 2.5 Hz), 155.9 (dd, $J_{C-F}$ = 247, 3.7 Hz), 173.3. EI-MS (m/z): 277.79, 279.80. (M⁺, Calcd for C₁₀H₉BrF₂O₂: 277.98, 279.97). |
| 30b | (4-bromo-2,6-difluorophenyl, methyl 2-arylpropanoate) | $^1$H-NMR (CDCl₃) δ: 1.50 (3H, d, J = 7.3 Hz), 3.70 (3H, s), 4.02 (1H, q, J = 7.2 Hz), 7.08 (1H, dt, J = 13.9, 3.2 Hz). $^{13}$C-NMR (CDCl₃) δ: 16.1, 34.2 (d, $J_{C-F}$ = 10.0 Hz), 52.4, 115.5 (dd, $J_{C-F}$ = 21.6, 5.0 Hz), 116.8 (t, $J_{C-F}$ = 18.7 Hz), 120.4 (t, $J_{C-F}$ = 12.5 Hz), 160.7 (dd, $J_{C-F}$ = 252, 8.7 Hz), 172.6 (d, $J_{C-F}$ = 1.2 Hz). FAB-MS (m/z): 278.02, 280.01 (M+, Calcd for C₁₀H₉BrF₂O₂: 277.98, 279.97). |
| 31a | (4-methyl-2,5-difluorophenyl, methyl 2-arylpropanoate) | $^1$H-NMR (CDCl₃) δ: 1.47 (3H, d, J = 7.1 Hz), 2.23 (3H, d, J = 1.8 Hz), 3.68 (3H, s), 3.96 (1H, q, J = 7.0 Hz), 6.86 (1H, dd, J = 9.9, 6.4 Hz), 6.94 (1H, dd, J = 9.7, 6.0 Hz). $^{13}$C-NMR (CDCl₃) δ: 14.4 (d, $J_{C-F}$ =3.7 Hz), 17.5, 38.0, 52.3 (d, $J_{C-F}$ = 3.7 Hz), 114.7 (dd, $J_{C-F}$ = 24.9, 5.0 Hz), 117.7 (dd, $J_{C-F}$ = 24.3, 5.6 Hz), 125.2 (dd, $J_{C-F}$ = 19.9, 7.5 Hz), 126.3 (dd, $J_{C-F}$ = 18.1, 6.9 Hz), 154.9 (dd, $J_{C-F}$ = 245, 2.5 Hz), 155.9 (dd, $J_{C-F}$ = 247, 1.9 Hz), 174.1. EI-MS (m/z): 214.01. (M⁺, Calcd for C₁₁H₁₂F₂O₂: 214.08). |
| 31b | (4-methyl-2,6-difluorophenyl, methyl 2-arylpropanoate) | $^1$H-NMR (CDCl₃) δ: 1.49 (3H, d, J = 7.3 Hz), 2.32 (3H, s), 3.69 (3H, s), 4.02 (1H, q, J = 7.3 Hz), 6.69 (2H, dt, J = 15.2, 3.0 Hz). $^{13}$C-NMR (CDCl₃) δ: 16.3 (d, $J_{C-F}$ = 3.7 Hz), 21.1 (d, $JC_F$ = 2.5 Hz), 34.1 (d, $J_{C-F}$ = 2.5 Hz), 52.2, 112.0 (dd, $J_{C-F}$ = 8.7, 4.4 Hz), 114.2 (t, $J_{C-F}$ = 18.7 Hz), 139.5 (t, $J_{C-F}$ = 10.0 Hz), 160.6 (dd, $J_{C-F}$ = 247, 8.7 Hz), 173.4. FAB-MS (m/z): 214.15. (M⁺, Calcd for C₁₁H₁₂F₂O₂: 214.08 |
| 32a | (4-bromomethyl-2,5-difluorophenyl, methyl 2-arylpropanoate) | $^1$H-NMR. (CDCl₃) δ: 1.49 (3H, d, J = 7.1 Hz), 3.70 (3H, s), 3.99 (1H, q, J = 7.3 Hz), 4.44 (2H, s), 7.03 (1H, dd, J = 9.9, 6.0 Hz), 7.09 (1H, dd, J = 9.5, 6.2 Hz). $^{13}$C-NMR (CDCl₃) δ: 17.5, 24.6 (d, $J_{C-F}$ = 3.7 Hz), 38.2, 52.4, 115.8 (dd, $J_{C-F}$ = 24.9, 3.7 Hz), 117.5 (dd, $J_{C-F}$ = 26.2, 3.7 Hz), 125.2 (dd, $J_{C-F}$ = 8.3, 4.2 Hz), 130.1 (dd, $J_{C-F}$ = 7.5, 3.7 Hz), 156.0 (dd, $J_{C-F}$ = 243, 2.5 Hz), 156.5 (dd, $J_{C-F}$ = 245, 2.5 Hz), 173.5. EI-MS (m/z): 291.97, 293.97. (M⁺, Calcd for C₁₁H₁₁BrF₂O₂: 291.99, 293.99). |

TABLE 5

| Compd. No. | Chemical Structure | Physical Data |
|---|---|---|
| 32b | (4-bromomethyl-2,6-difluorophenyl, methyl 2-arylpropanoate) | 1H-NMR (CDCl₃) δ: 1.52 (3H, d, J = 3.7 Hz), 3.71 (3H, s), 4.05 (1H, q, J = 7.4 Hz), 4.39 (2H, s), 7.13 (2H, dt, J = 15.4, 3.4 Hz). $^{13}$C-NMR (CDCl₃) δ: 19.5, 27.4 (d, $J_{C-F}$ = 3.7 Hz), 38.0, 52.5, 113.2 (dd, $J_{C-F}$ = 9.7, 5.8 Hz), 138.3 (t, $J_{C-F}$ = 10.0 Hz), 149.7, 151.8, 160.6 (dd, $J_{C-F}$ = 257, 8.7 Hz), 170.9. FAB-MS (m/z): 293.03, 295.04. (M⁺+H, Calcd for C₁₁H₁₂BrF₂O₂: 293.00, 295.00). |
| | (2-bromo-4-methyl-6-fluorobenzaldehyde) | $^1$H-NMR (CDCl₃) δ: 2.40 (3H1, s), 6.94 (1H, d, J = 11.4 Hz), 7.30 (1H, s), 10.3 (1H, brs). $^{13}$C-NMR (CDCl₃) δ: 21.3 (d, $J_{C-F}$ = 1.9 Hz), 116.8 (d, $J_{C-F}$ = 21.1 Hz), 116.8 (d, $J_{C-F}$ = 21.1 Hz), 120.1 (d, $J_{C-F,}$ = 9.3 Hz), 125.1 (d, $J_{C-F}$ = 3.7 Hz), 130.6 (d, $J_{C-F}$ = 3.1 Hz), 147.6 (d, $J_{C-F}$ = 9.9 Hz), 163.0 (d, $J_{C-F}$ = 265 Hz), 188.1. FAB-MS (m/z): 216.1, 218.2 (M⁺, Calcd for C₈H₆BrFO: 216.0, 218.0). |

TABLE 5-continued

| Compd. No. | Chemical Structure | Physical Data |
|---|---|---|
| 36 | H₃C-, Br, COOH, F (2-bromo-6-fluoro-4-methylphenylacetic acid) | $^1$H-NMR (CDCl$_3$) δ: 2.32 (3H, s), 3.86 (2H, d, J = 1.8 Hz), 6.87 (1H, d, J = 9.9 Hz), 7.21 (1H, s), 10.3 (1H, brs). $^{13}$C-NMR (CDCl$_3$) δ: 20.9 (d, J$_{C-F}$ = 1.9 Hz), 34.0 (d, J$_{C-F}$ = 3.1 Hz), 115.2 (d, J$_{C-F}$ = 23.0 Hz), 118.8 (d, J$_{C-F}$ = 18.6 Hz), 125.4 (d, J$_{C-F}$ = 5.0 Hz), 128.9 (d, J$_{C-F}$ = 3.1 Hz), 140.7 (d, J$_{C-F}$ = 8.7 Hz), 161.0 (d, J$_{C-F}$ = 250 Hz), 176.2. FAB-MS (m/z): 247.1, 249.1 (M$^+$+H, Calcd for C$_9$H$_9$BrFO$_2$: 247.0, 249.0). |
| 37 | H₃C-, Br, COOCH₃, F, CH₃ | $^1$H-NMR (CDCl$_3$) δ: 1.47 (3H, d, J = 7.0 Hz), 2.31 (3H, s), 3.69 (3H, s), 4.18 (1H, q, J = 7.2 Hz), 6.83 (1H, d, J = 11.0 Hz), 7.21 (1H, s). $^{13}$C-NMR (CDCl$_3$) δ: 15.7 (d, J$_{C-F}$ = 1.9 Hz), 20.7 (d, J$_{C-F}$ = 1.9 Hz), 40.8, 52.2, 115.8 (d, J$_{C-F}$ = 23.0 Hz), 124.1 (d, J$_{C-F}$ = 6.8 Hz), 126.2 (d, J$_{C-F}$ = 16.8 Hz), 129.1 (d, J$_{C-F}$ = 3.1 Hz), 139.8 (d, J$_{C-F}$ = 9.3 Hz), 160.5 (d, J$_{C-F}$ = 249 Hz), 173.5. FAB-MS (m/z): 275.1, 277.1 (M$^+$+H, Calcd for C$_{11}$H$_{13}$BrFO$_2$: 275.0, 277.0). |
| 38 | O, CO₂CH₃, Br, OCH₃, F, CH₃ (cyclopentanone-methyl ester with bromo-fluoro-methyl phenylacetate) | $^1$H-NMR (CDCl$_3$) δ: 1.47 (3H, d, J = 7.0 Hz), 1.69-1.82 (1H, m), 1.85-2.03 (2H, m), 2.09-2.21 (1H, m), 2.39-2.50 (2H, m), 2.95 (1H, dd, J = 13.9, 2.6 Hz), 3.20 (1H, dd, J = 13.9, 1.1 Hz), 3.69 (3H, s), 3.74 (3H, s), 4.18 (1H, q, J = 7.2 Hz), 6.83 (1H, dd, J = 11.0, 1.5 Hz), 7.17 (1H, brs). $^{13}$C-NMR (CDCl$_3$) δ 15.6 (d, J$_{C-F}$ = 1.9 Hz), 19.4, 31.8 (d, J$_{C-F}$ = 2.5 Hz), 37.9 (d, J$_{C-F}$ = 1.9 Hz), 38.0, 40.9, 52.3, 52.8, 61.3, 116.8 (dd, J$_{C-F}$ = 23.0, 1.2 Hz), 124.4 (d, J$_{C-F}$ = 5.6 Hz), 127.9 (d, J$_{C-F}$ = 16.8 Hz), 130.2 (d, J$_{C-F}$ = 3.1 Hz), 138.6 (dd; J$_{C-F}$ = 8.7, 1.2 Hz), 160.5 (d, J$_{C-F}$ = 250 Hz), 170.8, 173.2, 213.8 (d, J$_{C-F}$ = 1.9 Hz). FAB-MS (m/z): 415.3, 417.3 (M$^+$+H, Calcd for C$_{18}$H$_{21}$BrFO$_5$: 415.1, 417.1). |

TABLE 6

| Compd. No. | Chemical Structure | Property | Physical Data |
|---|---|---|---|
| 10a | HO-(cyclopentyl)-NH-Ar-CH(CH₃)COOH, F | clear yellow oil | $^1$H-NMR (CDCl$_3$) δ: 1.28 (3H, d, J = 7.3 Hz), 1.32-1.87 (5H, m), 2.03-2.15 (1H, m), 3.40 (1H, q, J = 4.4 Hz), 3.71 (1H, q, J = 7.3 Hz), 3.89 (1H, q, J = 3.3 Hz), 6.25-6.35 (2H, m), 6.90 (1H, t, J = 8.8 Hz). $^{13}$C-NMR (CDCl$_3$) δ: 18.1, 22.4, 31.5, 33.7, 39.0, 62.9, 78.3, 100.1, 110.2, 116.1, 129.8, 150.8, 162.7 (d, J$_{C-F}$ = 242 Hz), 178.5. HR-FAB-MS (m/z): 267.1274, (M$^+$, Calcd for C$_{14}$H$_{18}$FNO$_3$: 267.1271). |
| 10b | OH-(cyclohexyl)-NH-Ar-CH(CH₃)COOH, F | brown solid | $^1$H-NMR (CDCl$_3$) δ: 0.96-1.05 (1H, m), 1.08-1.22 (3H, m), 1.24 (3H, d, J = 6.2 Hz), 1.53-1.66 (2H, m), 1.89-1.99 (2H, m), 2.92-3.00 (1H, m), 3.24-3.32 (1H, m), 3.71 (1H, q, J = 7.3 Hz). 6.24-6.35 (2H, m). 6.90 (1H, t, J = 8.8 Hz). $^{13}$C-NMR (CDCl$_3$) δ: 18.1, 25.4, 25.6, 32.2, 34.9, 39.0, 59.9, 74.6, 100.4, 110.4, 116.2, 129.8, 151.0, 162.7 (d, J$_{C-F}$ = 241 Hz), 178.4. HR-FAB-MS (m/z): 281.1423 (M$^+$, Calcd for C$_{15}$H$_{20}$FNO$_3$: 281.1427). |
| 11a | cyclopentyl-NH-Ar-CH(CH₃)COOH, F | brown powder | $^1$H-NMR (CDCl$_3$) δ: 1.28 (6H, d, J = 7.0 Hz), 1.33-1.68 (6H, m), 1.79-1.91 (2H, m), 3.56-3.64 (1H, m), 3.70 (1H, q, J = 7.3 Hz), 6.17-6.30 (2H, m). 6.90 (1H, t, J = 8.8 Hz). $^{13}$C-NMR (CDCl$_3$) δ: 18.1, 25.0, 33.9, 39.0, 55.7, 100.3, 110.4, 116.1, 116.3, 129.8, 130.0, 150.8, 161.2 (d, J$_{C-F}$ = 242 Hz), 178.4. HR-FAB-MS (m/z): 251.1324 (M$^+$, Calcd for C$_{14}$H$_{18}$FNO$_2$: 251.1322). Anal. Calcd for C$_{14}$H$_{18}$FNO$_2$: C, 66.91; H, 7.22; N, 5.57. Found: C, 67.05; H, 7.24; N, 5,46. |

TABLE 6-continued

| Compd. No. | Chemical Structure | Property | Physical Data |
|---|---|---|---|
| 11b | (cyclohexyl-NH, F, CH(CH3)COOH phenyl) | brown powder | $^1$H-NMR (CDCl$_3$) δ: 0.99-1.27 (4H, m), 1.28 (3H, d, J = 8.8 Hz), 1.48-1.69 (4H, m), 1.86-1.91 (2H, m), 3.00-3.10 (1H, m), 3.70 (1H, q, J = 7.2 Hz), 6.16-6.28 (2H, m), 6.90 (1H, t, J = 8.8 Hz). $^{13}$C-NMR (CDCl$_3$) δ: 18.1, 26.1, 27.0, 34.1, 39.0, 52.9, 100.3, 100.7, 110.3, 116.1, 129.9, 130.0, 150.1, 162.7 (d, J$_{C-F}$ = 242 Hz), 178.5. HR-FAB-MS (m/z): 265.1481 (M$^+$, Calcd for C$_{15}$H$_{20}$FNO$_2$: 265.1478). Anal. Calcd for C$_{15}$H$_{20}$FNO$_2$: C, 67.90; H, 7.60; N, 5.28. Found: C, 67.97; H, 7.64; N, 5.28. |

TABLE 7

| Compd. No. | Chemical Structure | Property | Physical Data |
|---|---|---|---|
| 12 | (cyclopentanone-O-phenyl-F-CH(CH3)COOH) | yellow oil | $^1$H-NMR (CDCl$_3$) δ: 1.49 (d, 3H, J = 7.3 Hz), 1.89-2.50 (n, 6H), 3.98 (q, 1H, J = 7.3 Hz), 4.55 (t, 1H, J = 8.2 Hz), 6.67-6.76 (m, 2H), 7.20 (t, 1H, J =8.6 Hz). $^{13}$C-NMR (CDCl$_3$) δ: 17.2, 29.4, 35.1, 37.6, 37.7, 79.7, 103.5, 111.7, 120.0, 158.2, 162.3 (d, J$_{C-F}$ = 245 Hz), 179.6, 213.5. HR-FAB-MS (m/z): 266.0956, Calcd for C$_{14}$H$_{15}$FO$_4$: 266.0954). |
| 13 | (HO-cyclopentyl-O-phenyl-F-CH(CH3)COOH) | yellow solid | $^1$H-Nma (CDCl$_3$) δ: 1.49 (d, 3H, J = 7.3 Hz), 1.47-2.19 (n, 6H), 3.96 (q, 1H, J = 7.3 Hz), 4.27-4.31 (m, 1H), 4.45-4.48 (m, 1H), 6.60-6.69 (n, 2H), 7.19 (t, 1H, J = 8.4 Hz). $^{13}$C-NMR (CDCl$_3$) δ: 17.2, 21.2, 29.8, 32.7, 37.6, 37.7, 84.8, 103.3, 111.4, 119.1, 129.0, 158.4, 162.4 (d, J$_{C-F}$ = 245 Hz), 179.2. HR-FAB-MS (m/z): 268.1109, (M$^+$, Calcd for C$_{14}$H$_{17}$FO$_4$: 268.1111). |
| 14 | (cyclopentyl-O-phenyl-F-CH(CH3)COOH) | white solid | H-NMR (CDCl$_3$) δ: 1.41 (d, 1H, J = 7.2 Hz), 1.62-1.97 (m, 8H), (q, 1H, J = 7.2 Hz), 4.73-4.77 (m, 1H), 6.56-6.67 (m, 2H), (t, 1H, J = 8.7 Hz). $^{13}$C-NMR (CDCl$_3$) δ: 18.0, 24.9, 33.7, 33.8, 39.2, 80.8, 103.8, 112.5, 120.8, 130.0, 130.2, 160.1, 163.9 (d, J$_{C-F}$ = 245 Hz), 177.8. HR-FAB-MS (m/z): 252.1163 (M$^+$, Calcd for C$_{14}$H$_{17}$FO$_3$: 252.1162. Anal Calcd for C$_{14}$H$_{17}$FO$_3$: C, 66.65; H, 6.79. Found: C, 66.67; H, 6.72. |
| 15 | (cyclopentanone-S-phenyl-F-CH(CH3)COOH) | yellow iol | $^1$H-NMR (CDCl$_3$) δ: 1.50 (d, 3H, J = 7.3 Hz), 1.51-2.42 (n, 6H), 3.61 (t, 1H, J = 7.3 Hz), 4.00 (q, 1H, J = 7.3 Hz), 7.15-7.26 (m, 3H). $^{13}$C-NMR (CDCl$_3$) δ: 17.01, 20.33, 30.61, 36.45, 38.08, 51.94, 118.23 (d, J$_{C-F}$ = 11.2 Hz), 126.3, 127.4, 129.1, 134.9, 160.0 (d, J$_{C-F}$ = 249 Hz), 179.2, 213.8. HR-FAB-MS (m/z): 282.0724 (M+, Clcd for C14H15FO3S: 282.0726). |

TABLE 8

| Compd. No. | Chemical Structure | Property | Physical Data |
|---|---|---|---|
| 16 | (HO-cyclopentyl-S-phenyl-F-CH(CH3)COOH) | yellow oil | $^1$H-NMR (CDCl$_3$) δ: 1.51 (d, 3H, J = 7.3 Hz), 1.54-2.32 (m, 6H), 3.39-3.45 (m, 1H), 4.00 (q, 1H, J = 7.3Hz), 4.11-4.16 (m, 1H), 7.08-7.14 (m, 2H), 7.22 (t, 1H, J = 8.0 Hz). $^{13}$C-NMR (CDCl$_3$) δ: 45.1, 68.8, 30.9, 33.4, 37.9, 53.4, 116.5, 125.4, 129.0, 137.6, 164.2, 160.0 (d, J$_{C-F}$ = 249 Hz), 178.5. HR-FAB-MS (m/z): 284.0884 (M$^+$, Calcd for C$_{14}$H$_{17}$FO$_3$S: 284.0882). |
| 17 | (cyclopentyl-S-phenyl-F-CH(CH3)COOH) | white solid | $^1$H-NMR (CDCl$_3$) δ: 1.50 (d, 3H, J = 7.3 Hz), 1.56-2.12 (m, 8H), 3.56-3.61 (m, 1H), 4.00 (q, 1H, J = 7.3 Hz), 7.00-7.08 (m, 2H), 7.20 (t, 1H, J = 7.9 Hz). $^{13}$C-NMR (CDCl$_3$) δ: 17.09, 24.79, 33.46, 37.91, 37.95, 45.36, 115.79, 124.14, 124.24, 128.80, 138.97, 139.0, 161.87 (d, J$_{C-F}$ = 241 Hz), 179.22. HR-FAB-MS (m/z): 268.0936 (M$^+$, Calcd for C$_{14}$H$_{17}$FO$_2$S: 268.0933). Anal Calcd for |

TABLE 8-continued

| Compd. No. | Chemical Structure | Property | Physical Data |
|---|---|---|---|
| 21a | 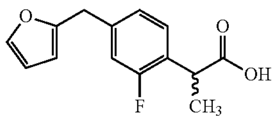 | white solid | $^1$H-NMR (CDCl$_3$) δ: 1.49 (3H, d, J = 7.1 Hz), 3.93 (2H, s), 4.01 (1H, q, J = 7.3 Hz), 6.04 (1H, dd, J = 3.1, 0.7 Hz), 6.29 (1H, dd, J = 3.1, 2.0 Hz), 6.92 (1H, dd, J = 10.8, 1.6 Hz), 6.99 (1H, dd, J = 7.9, 1.8 Hz), 7.23 (1H, t, J = 7.8 Hz), 7.33 (1H, dd, J = 0.9, 0.5 Hz). $^{13}$C-NMR (CDCl$_3$) δ 17.1, 33.8 (d, J$_{C-F}$ = 1.9 Hz), 38.1 (d, J$_{C-F}$ = 2.5 Hz), 106.6, 110.3, 115.7 (d, J$_{C-F}$ = 22.4 Hz), 124.5 (d, J$_{C-F}$ = 3.1 Hz), 125.1 (d, J$_{C-F}$ = 15.5 Hz), 128.7 (d, J$_{C-F}$ = 4.3 Hz), 139.7 (d, J$_{C-F}$ = 7.5 Hz), 141.7, 153.4, 160.3 (d, J$_{C-F}$ = 247 Hz), 179.9. HL-FAB-MS (m/z): 271.0743 (M$^+$+Na, Calcd for C$_{14}$H$_{13}$FO$_3$Na: 271.0753). Anal. Calcd for C$_{14}$H$_{13}$FO$_3$: C, 67.73; H, 5.28. Found: C, 67.46; H, 5.28. |
| 21b | 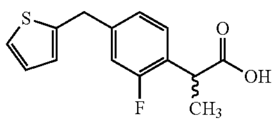 [SMILES: CC(C(=O)O)c1ccc(Cc2cccs2)cc1F] | white solid | $^1$H-NMR (CDCl$_3$) δ: 1.50 (3H, d, J = 7.3 Hz), 4.01 (1H, q, J = 7.2 Hz), 4.12 (2H, s), 6.81 (1H, dd, J = 3.5, 0.9 Hz), 6.90-6.94 (2H, m), 7.00 (1H, dd, J = 7.9, 1.6 Hz), 7.16 (1H, dd, J = 5.1, 1.1 Hz), 7.23 (1H, t, J = 7.9 Hz). $^{13}$C-NMR. (CDCl$_3$) δ: 17.1, 35.3 (d, J$_{C-F}$ = 1.9 Hz), 38.1 (d, J$_{C-F}$ = 3.1 Hz), 115.6 (d, J$_{C-F}$ = 23.0 Hz), 124.2, 124.4 (d, J$_{C-F}$ = 3.7 Hz), 125.1 (d, J$_{C-F}$ = 15.5 Hz), 125.5, 126.9, 128.7 (d, J$_{C-F}$ = 5.0 Hz), 141.9 (d, J$_{C-F}$ = 7.5 Hz), 142.6, 160.4 (d, J$_{C-F}$ = 247 Hz), 179.9. HL-FAB-MS (m/z): 287.0522 (M$^+$+Na, Calcd for C$_{14}$H$_{13}$FO$_2$SNa: 287.0518). Anal. Calcd for C$_{14}$H$_{13}$FO$_2$S: C, 63.62; H, 4.96. Found: C, 63.46; H, 5.14. |

TABLE 9

| Compd. No. | Chemical Structure | Property | Physical Data |
|---|---|---|---|
| 22a | 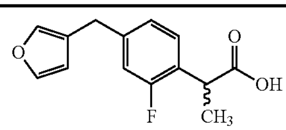 | white solid | 1H-NMR (CDCl$_3$) δ: 1.50 (3H, d, J = 7.3 Hz), 3.74 (2H, s), 4.01 (1H, q, J = 7.2 Hz), .6.23 (1H, d, J = 1.5 Hz), 6.89 (1H, dd, J = 11.0, 1.5 Hz), 6.97 (1H, dd, J = 8.1, 1.5 Hz), 7.22 (1H, t, J = 7.7 Hz), 7.24 (1H, d, J = 1.8 Hz), 7.36 (1H, t, J = 1.5 Hz). $^{13}$C-NMR (CDCl$_3$) δ: 17.1 (d, J$_{C-F}$ = 1.2 Hz), 30.5 (d, J$_{C-F}$ = 1.9 Hz), 38.1 (d, J$_{C-F}$ = 2.5 Hz), 111.1, 115.5 (d, J$_{C-F}$ = 22.4 Hz), 123.2, 124.4 (d, J$_{C-F}$ = 3.7 Hz), 124.8 (d, J$_{C-F}$ = 14.9 Hz), 128.6 (d, J$_{C-F}$ = 4.3 Hz), 139.7, 141.9 (d, J$_{C-F}$ = 7.5 Hz), 143.2, 160.4 (d, J$_{C-F}$ = 247 Hz), 180.0. HL-FAB-MS (m/z): 271.0769 (M$^+$+Na, Calcd for C$_{14}$H$_{13}$FO$_3$Na: 271.0746). Anal. Calcd for C$_{14}$H$_{13}$FO$_3$: C, 67.73; H, 5.28. Found: C, 67.67; H, 5.42. |
| 22b | 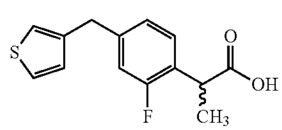 | white solid | $^1$H-NMR (CDCl$_3$) δ: 1.50 (3H, d, J = 7.1 Hz), 3.95 (2H, s), 4.01 (1H, q, J = 7.2 Hz), 6.82 (1H, dd, J = 8.2, 1.5 Hz), 6.90 (1H, d, J = 1.3 Hz), 6.96 (1H, dd, J = 7.8, 1.4 Hz), 7.22 (1H, t, J = 7.6 Hz), 7.26 (1H, t, J = 2.5 Hz). $^{13}$C-NMR (CDCl$_3$) δ: 17.1, 35.9 (d, J$_{C-F}$ = 1.2 Hz), 38.1 (d, J$_{C-F}$ = 2.5 Hz), 115.7 (d, J$_{C-F}$ = 22.4 Hz), 121.6, 124.6 (d, J$_{C-F}$ = 3.1 Hz), 124.7 (d, J$_{C-F}$ = 14.9 Hz), 125.9, 128.3, 128.6 (d, J$_{C-F}$ = 4.3 Hz), 140.3, 142.1 (d, J$_{C-F}$ = 7.5 Hz), 160.4 (d, J$_{C-F}$ = 247 Hz), 179.9. HL-FAB-MS (m/z): 287.0523 (M$^+$+Na, Calcd for C$_{14}$H$_{13}$FO$_2$SNa: 287.0518). Anal. Calcd for C$_{14}$H$_{13}$FO$_2$S: C, 63.62; H, 4.96. Found: C, 63.60; H, 5.10. |

TABLE 9-continued

| Compd. No. | Chemical Structure | Property | Physical Data |
|---|---|---|---|
| 23 | 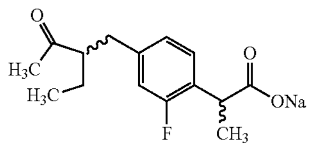 | clear colorless oil | $^1$H-NMR (CDCl$_3$) δ: 0.89 (3H, t, J = 7.5 Hz), 1.49 (3H, d, J = 7.3 Hz), 1.52-1.58 (1H, m), 1.60-1.70 (1H, m), 2.05 (3H, s), 2.63 (1H, q, J = 6.5 Hz), 2.69-2.78 (1H, m), 2.88 (1H, dd, J = 13.2, 7.20 (1H, t, J = 7.7 Hz), 10.9 (1H, brs). $^{13}$C-NMR. (CDCl$_3$) δ: 11.4, 17.1, 24.4, 30.0, 36.3 (d, J$_{C-F}$ = 1.9 Hz), 38.1 (d, J$_{C-F}$ = 3.1 Hz), 55.6, 115.8 (dd, J$_{C-F}$ = 21.7, 3.7 Hz), 124.8 (d, J$_{C-F}$ = 2.5 Hz), 124.9 (d, J$_{C-F}$ = 9.3 Hz), 128.6 (d, J$_{C-F}$ = 4.3 Hz), 141.3 (d, J$_{C-F}$ = 8.1 Hz), 160.2 (d, J$_{C-F}$ = 247 Hz), 179.8, 212.0. HL-FAB-MS (m/z): 289.1225 (M$^+$+Na, Calcd. for C$_{15}$H$_{19}$FO$_3$Na: 289.1216). |

TABLE 10

| Compd. No. | Chemical Structure | Property | Physical Data |
|---|---|---|---|
| 24 | 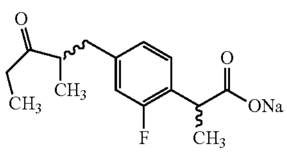 | clear colorless oil | $^1$H-NMR (CDCl$_3$) δ: 0.99 (3H, t, J = 7.3 Hz), 1.09 (3H, d, J = 7.3 Hz), 1.50 (3H, d, J = 7.3 Hz), 2.23-2.37 (1H, m), 2.45 (1H, q, J = 7.3 Hz), 2.53 (1H, dd, J = 12.8, 7.3 Hz), 2.82 (1H, q, J = 7.0 Hz), 2.97 (1H, dd, J = 6.8, 3.4 Hz), 4.00 (1H, q, J = 7.2 Hz), 6.85 (1H, dd, J = 11.0, 1.8 Hz), 6.90 (1H, dd, J = 8.1, 1.5 Hz), 7.21 (1H, t, J = 7.7 Hz), 10.8 (1H, brs).$^{13}$C-NMR (CDCl$_3$) δ: 7.53, 16.6, 17.1, 34.9, 38.1 (d, J$_{C-F}$ = 3.1 Hz), 38.3 (d, J$_{C-F}$ =1.2 Hz), 47.5, 115.7 (d, J$_{C-F}$ = 2.5 Hz), 115.9 (d, J$_{C-F}$ = 3.1 Hz), 124.8 (d, J$_{C-F}$ = 2.5 Hz), 128.5 (d, J$_{C-F}$ = 5.0 Hz), 141.3 (d, J$_{C-F}$ = 7.5 Hz), 160.2 (d, J$_{C-F}$ = 247 Hz), 179.9, 214.5. HL-FAB-MS (m/z): 289.1216 (M$^+$+Na, Calcd for C$_{15}$H$_{19}$FO$_3$Na: 289.1216). |
| 33a | 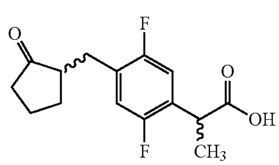 [SMILES: CC(C(=O)O)c1cc(F)c(CC2CCCC2=O)cc1F] | clear yellow oil | $^1$H-NMR (CDCl$_3$) δ: 1.50 (3H, d, J = 7.9 Hz), 1.47-1.61 (1H, m), 1.70-1.83 (1H, m), 1.94-2.05 (1H, m), 2.07-2.20 (2H, m), 2.32-2.42 (2H, m), 2.53 (1H, dd, J = 13.8, 9.4 Hz), 3.12 (1H, dd, J = 13.8, 3.2 Hz), 4.00 (1H, q, J = 7.2 Hz), 6.89 (1H, dd, J = 9.9, 6.2 Hz), 6.99 (1H, dd, J = 9.9, 6.0 Hz), 9.26 (1H, brs). $^{13}$C-NMR (CDCl$_3$) δ: 17.1 (d, J$_{C-F}$ = 5.0 Hz), 20.5, 28.4, 29.2, 37.9, 38.1, 49.8, 115.2 (dd, J$_{C-F}$ = 25.5, 4.4 Hz), 117.4 (dd, J$_{C-F}$ = 24.9, 2.5 Hz), 126.4 (dd, J$_{C-F}$ = 8.3, 4.2 Hz), 127.6 (dd, J$_{C-F}$ = 9.1, 4.6 Hz), 156.1 (dd, J$_{C-F}$ = 243, 2.5 Hz), 157.1 (dd, J$_{C-F}$ = 241, 1.9 Hz), 179.2, 219.8. HL-FAB-MS (m/z): 305.0959. (M$^+$+Na, Calcd for C$_{15}$H$_{16}$F$_2$NaO$_3$: 305.0965). |
| 33b | 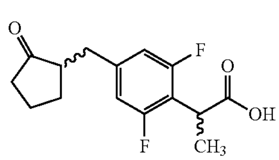 [SMILES: CC(C(=O)O)c1c(F)cc(CC2CCCC2=O)cc1F] | clear yellow oil | 1H-NMR (CDCl$_3$) δ: 1.50 (3H, d, J = 7.1 Hz), 1.45-1.59 (1H, m), 1.68-1.84 (1H, m), 1.94-2.05 (1H, m), 2.06-2.19 (2H, m), 2.27-2.42 (2H, m), 2.49 (1H, dd, J = 13.9, 9.3 Hz), 3.10 (1H, dd, J = 14.0, 4.1 Hz), 4.10 (1H, q, J = 7.2 Hz), 6.71 (2H, dt, J = 14.8, 2.9 Hz), 9.53 (1H, brs). $^{13}$C-NMR (CDCl$_3$) δ: 16.0, 20.5, 29.2, 34.2, 35.1, 38.0, 50.6, 111.8 (dd, J$_{C-F}$ = 8.3, 4.2 Hz), 114.4 (t, J$_{C-F}$ = 18.7 Hz), 142.1 (t, J$_{C-F}$ = 9.3 Hz), 160.7 (dd, J$_{C-F}$ = 248, 10.0 Hz), 178.6, 219.6. HL-FAB-MS (m/z): 305.0963. (M$^+$+Na, Calcd for C$_{15}$H$_{16}$F$_2$NaO$_3$: 305.0965). |

TABLE 11

| Compd. No. | Chemical Structure | Property | Physical Data |
|---|---|---|---|
| 39 | 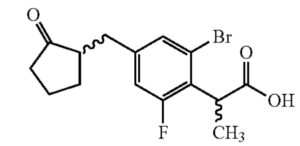 | clear yellow oil | $^1$H-NMR (CDCl$_3$) δ: 1.47 (3H, d, J = 7.0 Hz), 1.69-1.82 (1H, m), 1.85-2.03 (2H, m), 2.09-2.21 (1H, m), 2.39-2.50 (2H, m), 2.95 (1H, dd, J = 13.9, 2.6 Hz), 3.20 (1H, dd, J = 13.9, 1.1 Hz), 3.69 (3H, s), 3.74 (3H, s), 4.18 (1H, q, J = 7.2 Hz), 6.83 (1H, dd, J = 11.0, 1.5 Hz), 7.17 (1H, brs). $^{13}$C-NMR (CDCl$_3$) δ: 15.6 (d, $J_{C-F}$ = 1.9 Hz), 19.4, 31.8 (d, $J_{C-F}$ = 2.5 Hz), 37.9 (d, $J_{C-F}$ = 1.9 Hz), 38.0, 40.9, 52.3, 52.8, 61.3, 116.8 (dd, $J_{C-F}$ = 23.0, 1.2 Hz), 124.4 (d, $J_{C-F}$ = 5.6 Hz), 127.9 (d, $J_{C-F}$ = 16.8 Hz), 130.2 (d, $J_{C-F}$ =n3.1 Hz), 138.6 (dd, $J_{C-F}$ = 8.7, 1.2 Hz), 160.5 (d, J = 250 Hz), 170.8, 173.2, 213.8 (d, $J_{C-F}$ = 1.9 Hz). FAB-MS (m/z): 415.3, 417.3 (M$^+$+H, Calcd for C$_{18}$H$_{21}$BrFO$_5$: 415.1, 417.1). |
| 40 | 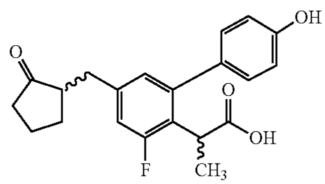 [SMILES: CC(C(=O)O)c1c(F)cc(CC2CCCC2=O)cc1-c1ccc(O)cc1] | white solid | $^1$H-NMR (CDCl$_3$) δ: 1.37 (3H, d, J = 6.2 Hz), 1.50-1.63 (1H, m), 1.69-1.83 (1H, m), 1.93-2.03 (1H, m), 2.08-2.20 (2H, m), 2.33-2.42 (2H, m), 2.51 (1H, dd, J = 13.4, 9.7 Hz), 3.12 (1H, dd, J = 13.9, 4.0 Hz), 3.86 (1H, q, J = 7.1 Hz), 6.83-6.88 (4H, m), 7.15 (2H, d, J = 8.4 Hz). $^{13}$C-NMR (CDCl$_3$) δ: 16.3 (d, $J_{C-F}$ = 2.5 Hz), 20.5, 293 (d, $J_{C-F}$ = 2.5 Hz), 35.0, 38.2, 38.4, 50.8, 114.9 (d, $J_{C-F}$ = 22.4 Hz), 115.32, 124.5 (d, $J_{C-F}$ = 14.3), 126.4 (d, $J_{C-F}$ = 1.9 Hz), 130.3, 132.2 (d, $J_{C-F}$ = 3.1 Hz), 140.3 (d, $J_{C-F}$ = 8.1 Hz), 143.5 (d, $J_{C-F}$ = 5.6 Hz), 155.5, 161.2 (d, $J_{C-F}$ = 247 Hz), 179.7, 221.3 (d, $J_{C-F}$ = 1.9 Hz). HR-FAB-MS (m/z): 356.1421 (M+, Calcd for C21H21FO4: 365.1424). Anal. Calcd for C$_{21}$H$_{21}$FO$_4$: C, 70.77; H, 5.94. Found: C, 70.63; H, 5.71. |

Test Example 1

Human Whole Blood Assay (In Vitro)

This test was carried out according to the method described in Inflamm. Res., 45: 68-74 (1996).
A: In Vitro COX-1 Assay As blood donors, persons who were healthy on the day of collecting and had not taken NSAIDs for at least a week or more were selected.

Blood was collected with no blood coagulation inhibitor and immediately used in the assay. Aliquots (500 µL) of collected blood were dispensed in respective tubes (Protein Lobingdin tube, Eppendorf Co. LTD., Tokyo, Japan). A solution (2 µL) of a test compound (final concentration: 0.1 µM to 1000 µM) in a suitable solvent (DMSO or MilliQ water) was added to the test tubes and incubated at 37° C. for 24 hours until blood coagulation was observed.

After the incubation, the sample was centrifuged at 12,000×g for 5 minutes to separate blood serum. To remove protein from blood, 100 µL of the obtained blood serum was added to 400 µL of ethanol, and the mixture was centrifuged again at 12,000×g for 5 minutes. TXB$_2$ in the supernatant was quantitatively determined using an enzyme immunoassay (EIA) kit [Cayman (Ann, Arbor, Mich., USA) #519031] according to the attached protocol.
B: In Vitro COX-2 Assay As blood donors, persons who were healthy on the day of collecting and had not taken NSAIDs for at least a week or more were selected.

Blood was collected in test tubes treated with heparin (Venoject II blood collection tubes, produced by TERUMO CORPORATION). To the test tubes, inflammatory stimulant lipopolysaccharide (LPS) [Sigma-Aldrich Japan Inc., #L2880 from E. coli 055:B5; diluted with phosphate buffered saline (PBS) at a final concentration of 100 µg/mL] was added. Aliquots of 500 µL were dispensed in the tubes, and 2 µL of a solution of a test compound (final concentration: 0.1 µM to 1000 µM) in a suitable solvent (DMSO or MilliQ water) was added to the tubes and incubated at 37° C. for 24 hours to induce COX-2.

After the incubation, the sample was centrifuged at 12,000×g for 5 minutes to separate blood serum. To remove protein from blood, 100 µL of obtained blood serum was added to 400 µL of ethanol, and the mixture was centrifuged again at 12,000×g for 5 minutes. PGE2 in the supernatant was quantitatively determined using an enzyme immunoassay (EIA) kit [Cayman (Ann, Arbor, Mich., USA) #514040] according to the attached protocol.
Statistical Analysis The measured values were expressed as the mean±S.E.M.

Tukey test and subsequent one-way or two-way analysis of variance (ANOVA) were carried out for evaluation among two or more groups.

The evaluation between two groups was based on Student's t-test, and the significant difference is p<0.05.

The results are shown in Table 12.

TABLE 12

| Test Compound | COX Inhibitory Activity IC$_{50}$(mM) | | COX Selectivity |
|---|---|---|---|
| | COX-1 | COX-2 | COX-1/COX-2 |
| 1 | 23.5 ± 4.8 | 10.1 ± 1.3 | 2.3 |
| 2 | 24.2 ± 8.6 | 14.3 ± 6.8 | 1.7 |
| 11a | 15.6 ± 0.5 | 21.3 ± 2.8 | 0.7 |
| 14 | 3.0 ± 0.2 | 26.3 ± 8.8 | 0.1 |
| 21a | 21.6 ± 7.5 | 4.1 ± 2.8 | 5.3 |
| 22a | 30.1 ± 8.6 | 4.0 ± 1.1 | 7.6 |

Test Example 2

Effect on Gastric Ulceration and Carrageenin-Induced Edema

A: Gastric Ulceration

This test was carried out according to the method described in Biochem. Pharmacol., 67; 575-85 (2004).

Male Wister rats (weight: 180 to 200 g) were fasted for 18 hours, and a test compound was orally administered to the rats. After 8 hours, the stomach was excised and the area of ulcers found in the stomach was measured. The total area of all ulcers was represented as the lesion index.

The results are shown in FIG. 1.

B: Effect on Carrageenin-Induced Edema

This test was carried out according to the method described in Br. J. Pharmacol., 151; 285-91 (2007).

Male Wister rats (weight: 180 to 200 g) were fasted for 18 hours, and a test compound was orally administered to the rats. After 1 hour, 100 µL of 1% carrageenin (dissolved in physiological saline) was subcutaneously injected into the left footpad to induce edema.

Before carrageenin administration, and three hours and six hours after carrageenin administration, the leg volume was measured using a plethysmometer.

The edema inhibition rate is calculated on the basis of the following equation.

Inhibition rate(%)=100−(edema volume when a compound was administrated/edema volume when a vehicle was administrated)×100.

Figure 2:
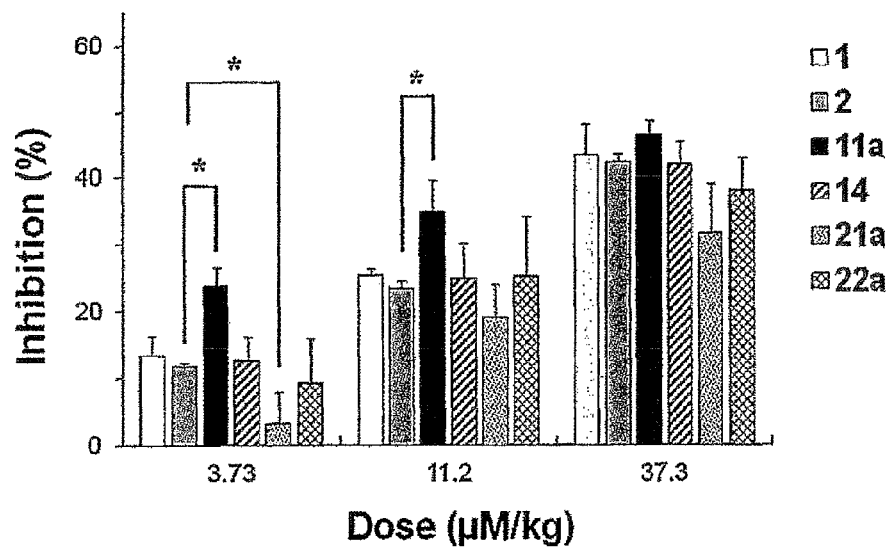
FIG. 2 includes figures illustrating the results of [B: Effect on Carrageenin-Induced Edema] in Test Example 2, where
Figure 2:
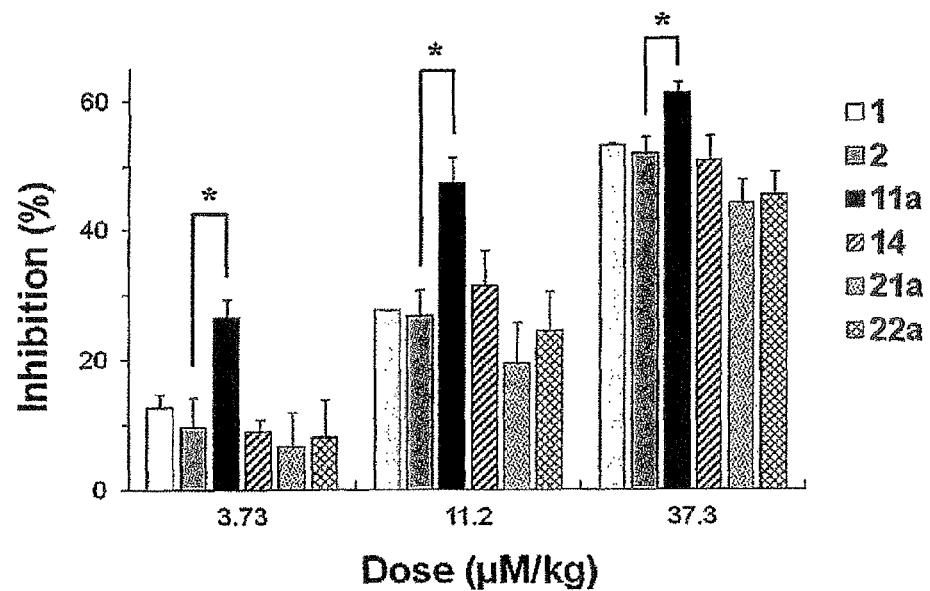

The results are shown in FIG. 2. FIG. 2A shows the inhibition rate 3 hours after administration, and FIG. 2B shows the inhibition rate 6 hours after administration.

Table 12, FIG. 1, and FIG. 2 indicate the following matters.

Compounds (11a) and (14) of the present invention have an excellent anti-inflammatory effect while having a weaker selective inhibitory action on COX-2 activity than loxoprofen (1), so that gastric ulceration was significantly reduced. This shows that compounds (11a) and (14) avoid a risk to cardiovascular system, such as myocardial infarction, while reducing gastric damage and having an excellent anti-inflammatory effect. In addition, compounds (21a) and (22a) of the present invention have the same level of anti-inflammatory effect as loxoprofen (1) while significantly reducing gastric damage.

As shown from these results, the 2-fluorophenyl propionic acid derivatives provided by the present invention have a favorable anti-inflammatory effect while avoiding ulceration as a side effect, which indicates that the pharmacological activity is successfully separated from the side effect.

Preparation Example 1

Tablet

| | |
|---|---|
| Compound 11a | 50 mg |
| Lactose | 100 mg |
| Hydroxypropyl cellulose | 150 mg |
| Magnesium stearate | 50 mg |

Based on the above prescription, granules were formulated and tableted to prepare a tablet having a weight of 350 mg according to a conventional method.

Preparation Example 2

Granules

| | |
|---|---|
| Compound 11a | 50 mg |
| Lactose | 100 mg |
| Corn starch cellulose | 150 mg |

Based on the above prescription, 200 mg of granules containing 50 mg of an active ingredient were prepared according to a conventional method.

INDUSTRIAL APPLICABILITY

As described above, the 2-fluorophenyl propionic acid derivatives provided by the present invention are novel compounds which have been hitherto unknown and which have no side effects such as gastrointestinal disorders, which are caused by conventional NSAIDs, and further have anti-inflammatory and analgesic effects stronger than those of loxoprofen, which has been clinically used. The 2-fluorophenyl propionic acid derivatives have a weaker selective inhibitory action on COX-2 activity, and thus can avoid a risk to cardiovascular system, such as myocardial infarction.

Accordingly, because of the wide margin of safety, the 2-fluorophenyl propionic acid derivatives are very effective in terms of safety for use in human and can make a great industrial contribution.

The invention claimed is:

1. A 2-fluorophenyl propionic acid derivative or a pharmaceutically acceptable salt thereof represented by formula (I-a):

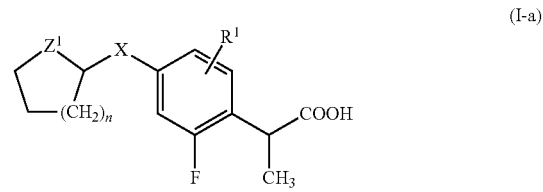

(I-a)

wherein
$R^1$ is a hydrogen atom,
X is —NH— or —O—,
$Z^1$ is —$CH_2$—, and n is 1.

2. A 2-fluorophenyl propionic acid derivative or a pharmaceutically acceptable salt thereof represented by formula (I-b):

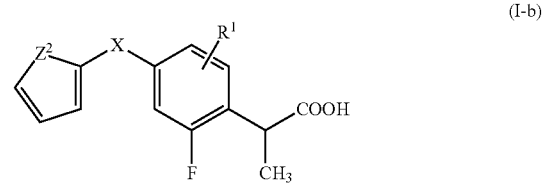

(I-b)

wherein
R¹ represents a hydrogen atom, a halogen atom, or a substituted or unsubstituted phenyl group,
X represents —CH₂—, —NH—, —O—, or —S—, and
Z² represents an oxygen atom or a sulfur atom.

3. A 2-fluorophenyl propionic acid derivative or a pharmaceutically acceptable salt thereof represented by formula (I-c):

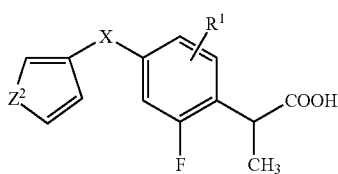

(I-c)

wherein
R¹ represents a hydrogen atom, a halogen atom, or a substituted or unsubstituted phenyl group,
X represents —CH₂—, —NH—, —O—, or —S—, and
Z² represents an oxygen atom or a sulfur atom.

4. A 2-fluorophenyl propionic acid derivative or a pharmaceutically acceptable salt thereof represented by formula (I-d):

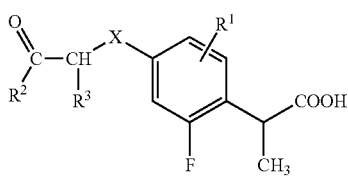

(I-d)

wherein R¹
represents a hydrogen atom, a halogen atom, or a substituted or unsubstituted phenyl group,
X represents —CH₂—, —NH—, —O—, or —S—, and
wherein R² and R³, which are the same or different, represent a lower alkyl group, and wherein $R_1$ does not represent hydrogen atom when X represents —CH₂—, respectively.

5. The 2-fluorophenyl propionic acid derivative or the pharmaceutically acceptable salt thereof according to claim 2, wherein the halogen atom of R¹ in the formula is selected from a chlorine atom, a bromine atom, a fluorine atom, and an iodine atom.

6. The 2-fluorophenyl propionic acid derivative or the pharmaceutically acceptable salt thereof according to claim 3, wherein the halogen atom of R¹ in the formula is selected from a chlorine atom, a bromine atom, a fluorine atom, and an iodine atom.

7. The 2-fluorophenyl propionic acid derivative or the pharmaceutically acceptable salt thereof according to claim 4, wherein the halogen atom of R¹ in the formula is selected from a chlorine atom, a bromine atom, a fluorine atom, and an iodine atom.

8. The 2-fluorophenyl propionic acid derivative or the pharmaceutically acceptable salt thereof according to claim 2, wherein the substituent of R¹ in the substituted phenyl group in the formula is a halogen atom or a hydroxyl group.

9. The 2-fluorophenyl propionic acid derivative or the pharmaceutically acceptable salt thereof according to claim 3, wherein the substituent of R¹ in the substituted phenyl group in the formula is a halogen atom or a hydroxyl group.

10. The 2-fluorophenyl propionic acid derivative or the pharmaceutically acceptable salt thereof according to claim 4, wherein the substituent of R¹ in the substituted phenyl group in the formula is a halogen atom or a hydroxyl group.

11. A medical drug comprising as an active ingredient the 2-fluorophenyl propionic acid derivative or the pharmaceutically acceptable salt thereof according to claim 1.

12. A medical drug comprising as an active ingredient the 2-fluorophenyl propionic acid derivative or the pharmaceutically acceptable salt thereof according to claim 2.

13. A medical drug comprising as an active ingredient the 2-fluorophenyl propionic acid derivative or the pharmaceutically acceptable salt thereof according to claim 3.

14. A medical drug comprising as an active ingredient the 2-fluorophenyl propionic acid derivative or the pharmaceutically acceptable salt thereof according to claim 4.

* * * * *